United States Patent
Egan et al.

(10) Patent No.: US 9,557,391 B2
(45) Date of Patent: Jan. 31, 2017

(54) APPARATUS AND METHOD FOR HIGH SENSITIVITY MAGNETOMETRY MEASUREMENT AND SIGNAL PROCESSING IN A MAGNETIC DETECTION SYSTEM

(71) Applicant: Lockheed Martin Corporation, Bethesda, MD (US)

(72) Inventors: Laird Nicholas Egan, Philadelphia, PA (US); David Nelson Coar, Cherry Hill, NJ (US); Jon C. Russo, Cherry Hill, NJ (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 15/003,590

(22) Filed: Jan. 21, 2016

(65) Prior Publication Data

US 2016/0216340 A1    Jul. 28, 2016

Related U.S. Application Data

(60) Provisional application No. 62/107,289, filed on Jan. 23, 2015.

(51) Int. Cl.
*G01R 33/02* (2006.01)
*G01R 33/032* (2006.01)
(Continued)

(52) U.S. Cl.
CPC ............. *G01R 33/032* (2013.01); *G01N 21/63* (2013.01); *G01N 22/00* (2013.01)

(58) Field of Classification Search
CPC ... G01R 33/032; G01R 33/1284; G01R 33/02; G01R 33/60; G01R 33/24; G01R 33/0094; G01N 21/63; G01N 22/00; G01N 24/10; G01N 2021/6421; G01N 21/6458; G01N 21/6486; G01N 21/6489; C30B 25/02; C30B 29/04
(Continued)

(56) References Cited

U.S. PATENT DOCUMENTS

| | | | |
|---|---|---|---|
| 2,746,027 A | 5/1956 | Murray | |
| 3,389,333 A | 6/1968 | Wolff, et al. | |

(Continued)

FOREIGN PATENT DOCUMENTS

| | | |
|---|---|---|
| DE | 69608006 T2 | 2/2001 |
| DE | 19600241 C2 | 8/2002 |

(Continued)

OTHER PUBLICATIONS

Acosta, "Optical Magnetometry with Nitrogen-Vacancy Centers in Diamond," University of California Berkeley, 2011.
(Continued)

*Primary Examiner* — Jay Patidar
(74) *Attorney, Agent, or Firm* — Foley & Lardner LLP

(57) ABSTRACT

A system for magnetic detection may include a nitrogen vacancy (NV) diamond material, a radio frequency (RF) excitation source, an optical excitation source, an optical detector, a magnetic field generator, and a controller. The controller may control the excitation sources to apply a first pulse sequence. The controller may receive a first light detection signal due to the first pulse sequence, measure first and second values of the first light detection signal at first and second reference periods, and compute a first measurement. The controller may further control the excitation sources to apply a second pulse sequence, receive a second light detection signal due to the second pulse sequence, measure first and second values of the second light detection signal at first and second reference periods, and compute a (Continued)

second measurement. The first and second measurements may be based on high and low resonance frequencies of the NV diamond material.

20 Claims, 10 Drawing Sheets

(51) Int. Cl.
  *G01N 21/63* (2006.01)
  *G01N 22/00* (2006.01)
(58) Field of Classification Search
  USPC .................................................. 324/244.1
  See application file for complete search history.

(56) References Cited

U.S. PATENT DOCUMENTS

| | | | |
|---|---|---|---|
| 3,514,723 A | 5/1970 | Cutler | |
| 3,518,531 A | 6/1970 | Huggett | |
| 3,745,452 A | 7/1973 | Osburn et al. | |
| 3,899,758 A | 8/1975 | Maier et al. | |
| 4,078,247 A | 3/1978 | Albrecht | |
| 4,084,215 A | 4/1978 | Willenbrock | |
| 4,329,173 A | 5/1982 | Culling | |
| 4,368,430 A | 1/1983 | Dale et al. | |
| 4,514,083 A | 4/1985 | Fukuoka | |
| 4,588,993 A | 5/1986 | Babij et al. | |
| 4,638,324 A | 1/1987 | Hannan | |
| 4,675,522 A | 6/1987 | Arunkumar | |
| 4,945,305 A | 7/1990 | Blood | |
| 5,019,721 A | 5/1991 | Martens et al. | |
| 5,038,103 A | 8/1991 | Scarzello et al. | |
| 5,113,136 A | 5/1992 | Hayashi et al. | |
| 5,134,369 A | 7/1992 | Lo et al. | |
| 5,189,368 A | 2/1993 | Chase | |
| 5,245,347 A | 9/1993 | Bonta et al. | |
| 5,252,912 A | 10/1993 | Merritt et al. | |
| 5,301,096 A | 4/1994 | Klontz et al. | |
| 5,384,109 A | 1/1995 | Klaveness et al. | |
| 5,396,802 A | 3/1995 | Moss | |
| 5,568,516 A | 10/1996 | Strohallen et al. | |
| 5,694,375 A | 12/1997 | Woodall | |
| 5,818,352 A | 10/1998 | McClure | |
| 5,907,420 A | 5/1999 | Chraplyvy et al. | |
| 6,057,684 A | 5/2000 | Murakami et al. | |
| 6,124,862 A | 9/2000 | Boyken et al. | |
| 6,130,753 A | 10/2000 | Hopkins et al. | |
| 6,195,231 B1 | 2/2001 | Sedlmayr et al. | |
| 6,360,173 B1 | 3/2002 | Fullerton | |
| 6,398,155 B1 | 6/2002 | Hepner et al. | |
| 6,433,944 B1 | 8/2002 | Nagao et al. | |
| 6,504,365 B2 | 1/2003 | Kitamura | |
| 6,542,242 B1 | 4/2003 | Yost et al. | |
| 6,636,146 B1 | 10/2003 | Wehoski | |
| 6,686,696 B2 | 2/2004 | Mearini et al. | |
| 6,690,162 B1 | 2/2004 | Schopohl et al. | |
| 7,118,657 B2 | 10/2006 | Golovchenko et al. | |
| 7,221,164 B1 | 5/2007 | Barringer | |
| 7,277,161 B2 | 10/2007 | Claus | |
| 7,305,869 B1 | 12/2007 | Berman et al. | |
| 7,307,416 B2 | 12/2007 | Islam et al. | |
| RE40,343 E | 5/2008 | Anderson | |
| 7,413,011 B1 | 8/2008 | Chee et al. | |
| 7,427,525 B2 | 9/2008 | Santori et al. | |
| 7,448,548 B1 | 11/2008 | Compton | |
| 7,471,805 B2 | 12/2008 | Goldberg | |
| 7,474,090 B2 | 1/2009 | Islam et al. | |
| 7,543,780 B1 | 6/2009 | Marshall et al. | |
| 7,546,000 B2 | 6/2009 | Spillane et al. | |
| 7,983,812 B2 | 7/2011 | Potter | |
| 8,120,351 B2 | 2/2012 | Rettig et al. | |
| 8,120,355 B1 | 2/2012 | Stetson | |
| 8,138,756 B2 | 3/2012 | Barclay et al. | |
| 8,294,306 B2 | 10/2012 | Kumar et al. | |
| 8,311,767 B1 | 11/2012 | Stetson | |
| 8,334,690 B2 | 12/2012 | Kitching et al. | |
| 8,415,640 B2 | 4/2013 | Babinec et al. | |
| 8,471,137 B2 | 6/2013 | Adair et al. | |
| 8,480,653 B2 | 7/2013 | Birchard et al. | |
| 8,525,516 B2 | 9/2013 | Le Prado et al. | |
| 8,547,090 B2 | 10/2013 | Lukin et al. | |
| 8,574,536 B2 | 11/2013 | Boudou et al. | |
| 8,575,929 B1 | 11/2013 | Wiegert | |
| 8,686,377 B2 | 4/2014 | Twitchen et al. | |
| 8,758,509 B2 | 6/2014 | Twitchen et al. | |
| 8,803,513 B2 | 8/2014 | Hosek et al. | |
| 8,885,301 B1 | 11/2014 | Heidmann | |
| 8,913,900 B2 | 12/2014 | Lukin et al. | |
| 8,947,080 B2 | 2/2015 | Lukin et al. | |
| 9,157,859 B2 | 10/2015 | Walsworth et al. | |
| 2002/0167306 A1 | 11/2002 | Zalunardo et al. | |
| 2003/0058346 A1 | 3/2003 | Bechtel et al. | |
| 2003/0076229 A1 | 4/2003 | Blanpain et al. | |
| 2003/0235136 A1 | 12/2003 | Akselrod et al. | |
| 2004/0013180 A1 | 1/2004 | Giannakis et al. | |
| 2004/0022179 A1 | 2/2004 | Giannakis et al. | |
| 2004/0042150 A1 | 3/2004 | Swinbanks et al. | |
| 2004/0109328 A1 | 6/2004 | Dahl et al. | |
| 2004/0247145 A1 | 12/2004 | Luo et al. | |
| 2005/0099177 A1 | 5/2005 | Greelish | |
| 2005/0126905 A1 | 6/2005 | Golovchenko et al. | |
| 2005/0130601 A1 | 6/2005 | Palermo et al. | |
| 2005/0134257 A1 | 6/2005 | Etherington et al. | |
| 2005/0146327 A1 | 7/2005 | Jakab | |
| 2006/0054789 A1 | 3/2006 | Miyamoto et al. | |
| 2006/0062084 A1 | 3/2006 | Drew | |
| 2006/0071709 A1 | 4/2006 | Maloberti et al. | |
| 2007/0004371 A1 | 1/2007 | Okanobu | |
| 2007/0247147 A1 | 10/2007 | Xiang et al. | |
| 2008/0016677 A1 | 1/2008 | Creighton, IV | |
| 2008/0048640 A1 | 2/2008 | Hull et al. | |
| 2008/0078233 A1 | 4/2008 | Larson et al. | |
| 2008/0089367 A1 | 4/2008 | Srinivasan et al. | |
| 2008/0204004 A1 | 8/2008 | Anderson | |
| 2008/0217516 A1 | 9/2008 | Suzuki et al. | |
| 2008/0239265 A1 | 10/2008 | Den Boef | |
| 2008/0299904 A1 | 12/2008 | Yi et al. | |
| 2009/0042592 A1 | 2/2009 | Cho et al. | |
| 2009/0060790 A1 | 3/2009 | Okaguchi et al. | |
| 2009/0079426 A1 | 3/2009 | Anderson | |
| 2009/0132100 A1 | 5/2009 | Shibata | |
| 2009/0277702 A1 | 11/2009 | Kanada et al. | |
| 2009/0310650 A1 | 12/2009 | Chester et al. | |
| 2010/0045269 A1 | 2/2010 | Lafranchise et al. | |
| 2010/0134922 A1 | 6/2010 | Yamada et al. | |
| 2010/0157305 A1 | 6/2010 | Henderson | |
| 2010/0188081 A1 | 7/2010 | Lammegger | |
| 2010/0237149 A1 | 9/2010 | Olmstead | |
| 2010/0271016 A1 | 10/2010 | Barclay et al. | |
| 2010/0308813 A1 | 12/2010 | Lukin et al. | |
| 2010/0315079 A1* | 12/2010 | Lukin ................. G01R 33/032 324/244.1 |
| 2010/0326042 A1 | 12/2010 | McLean et al. | |
| 2011/0034393 A1 | 2/2011 | Justen et al. | |
| 2011/0062957 A1 | 3/2011 | Fu et al. | |
| 2011/0063957 A1 | 3/2011 | Isshiki et al. | |
| 2011/0066379 A1 | 3/2011 | Mes | |
| 2011/0127999 A1 | 6/2011 | Lott et al. | |
| 2011/0165862 A1 | 7/2011 | Yu et al. | |
| 2011/0243267 A1 | 10/2011 | Won et al. | |
| 2012/0016538 A1 | 1/2012 | Waite et al. | |
| 2012/0019242 A1 | 1/2012 | Hollenberg et al. | |
| 2012/0037803 A1 | 2/2012 | Strickland | |
| 2012/0044014 A1 | 2/2012 | Stratakos et al. | |
| 2012/0051996 A1 | 3/2012 | Scarsbrook et al. | |
| 2012/0063505 A1 | 3/2012 | Okamura et al. | |
| 2012/0087449 A1 | 4/2012 | Ling et al. | |
| 2012/0140219 A1 | 6/2012 | Cleary | |
| 2012/0181020 A1 | 7/2012 | Barron et al. | |
| 2012/0194068 A1 | 8/2012 | Cheng et al. | |
| 2012/0257683 A1 | 10/2012 | Schwager et al. | |
| 2012/0281843 A1 | 11/2012 | Christensen et al. | |
| 2012/0326793 A1 | 12/2012 | Gan | |

(56) References Cited

U.S. PATENT DOCUMENTS

| | | |
|---|---|---|
| 2013/0066448 A1 | 3/2013 | Alonso |
| 2013/0127518 A1 | 5/2013 | Nakao |
| 2013/0215712 A1 | 8/2013 | Geiser et al. |
| 2013/0265782 A1 | 10/2013 | Barrena et al. |
| 2014/0012505 A1 | 1/2014 | Smith et al. |
| 2014/0037932 A1 | 2/2014 | Twitchen et al. |
| 2014/0061510 A1 | 3/2014 | Twitchen et al. |
| 2014/0072008 A1 | 3/2014 | Faraon et al. |
| 2014/0077231 A1 | 3/2014 | Twitchen et al. |
| 2014/0081592 A1 | 3/2014 | Bellusci et al. |
| 2014/0104008 A1 | 4/2014 | Gan |
| 2014/0126334 A1 | 5/2014 | Megdal et al. |
| 2014/0139322 A1 | 5/2014 | Wang et al. |
| 2014/0166904 A1 | 6/2014 | Walsworth et al. |
| 2014/0167759 A1 | 6/2014 | Pines et al. |
| 2014/0168174 A1 | 6/2014 | Idzik et al. |
| 2014/0191139 A1 | 7/2014 | Englund |
| 2014/0191752 A1 | 7/2014 | Walsworth et al. |
| 2014/0198463 A1 | 7/2014 | Klein |
| 2014/0215985 A1 | 8/2014 | Pollklas |
| 2014/0247094 A1 | 9/2014 | Englund et al. |
| 2014/0272119 A1 | 9/2014 | Kushalappa et al. |
| 2014/0273826 A1 | 9/2014 | Want et al. |
| 2014/0306707 A1 | 10/2014 | Walsworth et al. |
| 2014/0327439 A1 | 11/2014 | Cappellaro et al. |
| 2014/0335339 A1 | 11/2014 | Dhillon et al. |
| 2014/0340085 A1 | 11/2014 | Cappellaro et al. |
| 2014/0368191 A1 | 12/2014 | Goroshevskiy et al. |
| 2015/0001422 A1 | 1/2015 | Englund et al. |
| 2015/0009003 A1 | 1/2015 | Ozawa et al. |
| 2015/0009746 A1 | 1/2015 | Kucsko et al. |
| 2015/0018018 A1 | 1/2015 | Shen et al. |
| 2015/0048822 A1 | 2/2015 | Walsworth et al. |
| 2015/0054355 A1 | 2/2015 | Ben-Shalom et al. |
| 2015/0090033 A1 | 4/2015 | Budker et al. |
| 2015/0128431 A1 | 5/2015 | Kuo |
| 2015/0137793 A1 | 5/2015 | Englund et al. |
| 2015/0158383 A1 | 6/2015 | Mastie et al. |
| 2015/0192532 A1 | 7/2015 | Clevenson et al. |
| 2015/0192596 A1 | 7/2015 | Englund et al. |
| 2015/0225052 A1 | 8/2015 | Cordell |
| 2015/0235661 A1 | 8/2015 | Heidmann |
| 2015/0253355 A1 | 9/2015 | Grinolds et al. |
| 2015/0268373 A1 | 9/2015 | Meyer |
| 2015/0269957 A1 | 9/2015 | El Hallak et al. |
| 2015/0276897 A1 | 10/2015 | Leussler et al. |
| 2015/0299894 A1 | 10/2015 | Markham et al. |
| 2015/0374250 A1 | 12/2015 | Hatano et al. |

FOREIGN PATENT DOCUMENTS

| | | |
|---|---|---|
| DE | 10228536 A1 | 1/2003 |
| EP | 0 161 940 B1 | 12/1990 |
| EP | 0 718 642 | 6/1996 |
| EP | 0 726 458 | 8/1996 |
| EP | 1 505 627 | 2/2005 |
| EP | 1 685 597 | 8/2006 |
| EP | 1 990 313 | 11/2008 |
| EP | 2 163 392 | 3/2010 |
| EP | 2 495 166 A1 | 9/2012 |
| EP | 2 587 232 A1 | 5/2013 |
| EP | 2 705 179 | 3/2014 |
| EP | 2 707 523 | 3/2014 |
| EP | 2 745 360 | 6/2014 |
| EP | 2 769 417 | 8/2014 |
| EP | 2 790 031 | 10/2014 |
| EP | 2 837 930 | 2/2015 |
| EP | 2 907 792 | 8/2015 |
| GB | 2 433 737 | 7/2007 |
| GB | 2 482 596 | 2/2012 |
| GB | 2 483 767 | 3/2012 |
| GB | 2 486 794 | 6/2012 |
| GB | 2 490 589 | 11/2012 |
| GB | 2 491 936 | 12/2012 |
| GB | 2 493 236 | 1/2013 |
| GB | 2 495 632 A | 4/2013 |
| GB | 2 497 660 | 6/2013 |
| GB | 2 510 053 A | 7/2014 |
| GB | 2 515 226 | 12/2014 |
| GB | 2 522 309 | 7/2015 |
| GB | 2 526 639 | 12/2015 |
| JP | 3782147 B2 | 6/2006 |
| JP | 4800896 B2 | 10/2011 |
| JP | 2012-103171 | 5/2012 |
| JP | 2012-110489 | 6/2012 |
| JP | 2012-121748 | 6/2012 |
| JP | 2013-028497 | 2/2013 |
| JP | 5476206 B2 | 4/2014 |
| JP | 5522606 B2 | 6/2014 |
| JP | 5536056 B2 | 7/2014 |
| JP | 5601183 B2 | 10/2014 |
| JP | 2014-215985 | 11/2014 |
| JP | 2014-216596 | 11/2014 |
| JP | 2015-518562 A | 7/2015 |
| JP | 5764059 B2 | 8/2015 |
| JP | 2015-167176 | 9/2015 |
| JP | 2015-529328 | 10/2015 |
| JP | 5828036 B2 | 12/2015 |
| JP | 5831947 B2 | 12/2015 |
| WO | WO-87/04028 | 7/1987 |
| WO | WO-88/04032 A1 | 6/1988 |
| WO | WO-95/33972 | 12/1995 |
| WO | WO-2011/046403 A2 | 4/2011 |
| WO | WO-2011/153339 | 12/2011 |
| WO | WO-2012/016977 A2 | 2/2012 |
| WO | WO-2012/084750 | 6/2012 |
| WO | WO-2013/066448 | 5/2013 |
| WO | WO-2013/093136 | 6/2013 |
| WO | WO-2013/188732 A1 | 12/2013 |
| WO | WO-2014/099110 A2 | 6/2014 |
| WO | WO-2014/135544 A1 | 9/2014 |
| WO | WO-2014/135547 A1 | 9/2014 |
| WO | WO-2014/166883 | 10/2014 |
| WO | WO-2014/210486 A1 | 12/2014 |
| WO | WO-2015/015172 | 2/2015 |
| WO | WO-2015/193156 A1 | 12/2015 |

OTHER PUBLICATIONS

Acosta, et al., "Diamonds with a high density of nitrogen—vacancy centers for magnetometry applications," Physical Review B, Sep. 2009.

Acosta, et al., "Nitrogen-vacancy centers: physics and applications," MRS Bulletin, 2013.

Aiello, et al., "Composite-pulse magnetometry with a solid-state quantum sensor," Nature Communications, Jan. 2013.

Alam, "Solid-state C-13 magic angle spinning NMR spectroscopy characterization of particle size structural variations in synthetic nanodiamonds," Materials Chemistry and Physics, Jun. 2004.

Albrecht, et al., "Coupling of nitrogen vacancy centres in nanodiamonds by means of phonons," New Journal of Physics, Aug. 2013.

Anthony, et al., "Jahn-Teller Splitting and Zeeman Effect of Acceptors in Diamond," 20th International Conference on Defects in Semiconductors, Jul. 1999.

Appel, et al., "Nanoscale microwave imaging with a single electron spin in diamond," New Journal of Physics, Nov. 2015.

Arai, et al., "Fourier magnetic imaging with nanoscale resolution and compressed sensing speed-up using electronic spins in diamond," Nature Nanotechnology, Oct. 2015.

Aslam, et al., "Single spin optically detected magnetic resonance with 60-90 GHz (E-band) microwave resonators," Review of Scientific Instruments, Jun. 2015.

Awschalom, et al., "Diamond age of spintronics," Scientific American, Oct. 2007.

Babamoradi, et al., "Correlation between entanglement and spin density in nitrogen-vacancy center of diamond," European Physical Journal D, Dec. 2011.

Babunts, et al., "Diagnostics of NV defect structure orientation in diamond using optically detected magnetic resonance with a modulated magnetic field," Technical Physics Letters, Jun. 2015.

(56) References Cited

OTHER PUBLICATIONS

Babunts, et al., "Temperature-scanned magnetic resonance and the evidence of two-way transfer of a nitrogen nuclear spin hyperfine interaction in coupled NV-N pairs in diamond," JETP Letters, Jun. 2012.
Bagguley, et al., "Zeeman effect of acceptor states in semiconducting diamond," Journal of the Physical Society of Japan, 1966.
Balasubramanian, et al., "Nanoscale imaging magnetometry with diamond spins under ambient conditions," Nature, Oct. 2008.
Balmer, et al., "Chemical Vapour deposition synthetic diamond: materials technology and applications," J. Of Physics, 2009.
Baranov, et al., "Enormously High Concentrations of Fluorescent Nitrogen-Vacancy Centers Fabricated by Sintering of Detonation Nanodiamonds," Small, Jun. 2011.
Barfuss, et al., "Strong mechanical driving of a single electron spin," Nature Physics, Oct. 2015.
Bennett, et al., "CVD Diamond for High Power Laser Applications," Proceedings of SPIE, Jan. 2013.
Berman & Chernobrod, "Single-spin microscope with sub-nanoscale resolution based on optically detected magnetic resonance," Proceedings of SPIE, May 2010.
Blakley, et al., "Room-temperature magnetic gradiometry with fiber-coupled nitrogen—vacancy centers in diamond," Optics Letters, Aug. 2015.
Bourgeois, et al., "Photoelectric detection of electron spin resonance of nitrogen-vacancy centres in diamond," Nature Communications, Oct. 2015.
Budker & Kimball, "Optical Magnetometry," Cambridge Press, 2013.
Budker & Romalis, "Optical Magnetometry," Nature Physics, 2007.
Casanova, et al., "Effect of magnetic field on phosphorus centre in diamond," Physica Status Solidi A, Jul. 2001.
Castelletto, et al., "Frontiers in diffraction unlimited optical methods for spin manipulation, magnetic field sensing and imaging using diamond nitrogen vacancy defects," Nanophotonics, 2012.
Chapman, et al., "Anomalous saturation effects due to optical spin depolarization in nitrogen-vacancy centers in diamond nanocrystals," Physical Review B, Jul. 2012.
Chen, et al., "Vector magnetic field sensing by a single nitrogen vacancy center in diamond," EPL, Mar. 2013.
Chernobrod, et al., "Improving the sensitivity of frequency modulation spectroscopy using nanomechanical cantilevers," Applied Physics Letters, 2004.
Chernobrod, et al., "Spin Microscope Based on Optically Detected Magnetic Resonance," Journal of Applied Physics, 2005.
Childress, et al., "Coherent dynamics of coupled electron and nuclear spin qubits in diamond," Science, 2006.
Chipaux, et al., "Magnetic imaging with an ensemble of nitrogen vacancy -centers in diamond," European Physical Journal D, Jul. 2015.
Chipaux, et al., "Nitrogen vacancies (NV) centers in diamond for magnetic sensors and quantum sensing," Proceedings of SPIE, Jan. 2015.
Chipaux, et al., "Wide bandwidth instantaneous radio frequency spectrum analyzer based on nitrogen vacancy centers in diamond," Applied Physics Letters, Dec. 2015.
Clevenson, et al., "Broadband magnetometry and temperature sensing with a light-trapping diamond waveguide," Nature Physics, May 2015.
Cooper, et al., " Time-resolved magnetic sensing with electronic spins in diamond," Nature Communications, Jan. 2014.
Creedon, et al., "Strong coupling between P1 diamond impurity centers and a three-dimensional lumped photonic microwave cavity," Physical Review B, Apr. 2015.
Davies, "Current problems in diamond: towards a quantitative understanding," Physica B—Condensed Matter, Dec. 1999.
De Lange, et al., "Single-Spin Magnetometry with Multipulse Sensing Sequences," Physical Review Letters, Feb. 2011.
Degen, "Scanning magnetic field microscope with a diamond single-spin sensor ," Applied Physics Letters, 2008.
Delacroix, et al., "Design, manufacturing, and performance analysis of mid-infrared achromatic half-wave plates with diamond subwavelength gratings," Applied Optics, 2012.
Denatale, et al., "Fabrication and characterization of diamond moth eye antireflective surfaces on Ge," J. Of Applied Physics, 1982.
Dobrovitski, et al., "Quantum Control over Single Spins in Diamond," Annual Review of Condensed Matter Physics vol. 4, 2013.
Doherty, et al., "The nitrogen-vacancy colour centre in diamond," Physics Reports, Jul. 2013.
Doherty, et al., "Theory of the ground-state spin of the Nv- center in diamond," Physical Review B, May 2012.
Doi, et al., "Pure negatively charged state of the Nv center in n-type diamond," Physical Review B, Feb. 2016.
Drake, et al., "Influence of magnetic field alignment and defect concentration on nitrogen-vacancy polarization in diamond," New Journal of Physics, Jan. 2016.
Dreau, et al., "Avoiding power broadening in optically detected magnetic resonance of single NV defects for enhanced dc magnetic field sensitivity," Physical Review B, Nov. 2011.
Dreau, et al., "High-resolution spectroscopy of single NV defects coupled with nearby C-13 nuclear spins in diamond," Physical Review B, Apr. 2012.
Dumeige, et al., "Magnetometry with nitrogen-vacancy ensembles in diamond based on infrared absorption in a doubly resonant optical cavity," Physical Review B, Apr. 2013.
Epstein, et al., "Anisotropic interactions of a single spin and dark-spin spectroscopy in diamond," Center for Spintronics and Quantum Computation, 2005.
Fedotov, et al., "High-resolution magnetic field imaging with a nitrogen-vacancy diamond sensor integrated with a photonic-crystal fiber," Optics Letters, Feb. 2016.
Fedotov, et al., "Photonic-crystal-fiber-coupled photoluminescence interrogation of nitrogen vacancies in diamond nanoparticles," Laser Physics Letters, Feb. 2012.
Feng & Wei, "A steady-state spectral method to fit microwave absorptions of NV centers in diamonds: application to sensitive magnetic field sensing," Measurement Science & Technology, Oct. 2014.
Freitas, et al., "Solid-State Nuclear Magnetic Resonance (NMR) Methods Applied to the Study of Carbon Materials," Chemistry and Physics of Carbon, vol. 31, 2012.
Geiselmann, et al., "Fast optical modulation of the fluorescence from a single nitrogen-vacancy centre," Nature Physics, Dec. 2013.
Gombert & Blasi, "The Moth-Eye Effect-From Fundamentals to Commercial Exploitation," Functional Properties of Bio-Inspired Surfaces, Nov. 2009.
Gong, et al., "Generation of Nitrogen-Vacancy Center Pairs in Bulk Diamond by Molecular Nitrogen Implantation," Chinese Physics Letters, Feb. 2016.
Gould, et al., "An imaging magnetometer for bio-sensing based on nitrogen-vacancy centers in diamond," Proceedings of the SPIE—Progress in Biomedical Optics and Imaging, 2014.
Gould, et al., "Room-temperature detection of a single 19 nm super-paramagnetic nanoparticle with an imaging magnetometer," Applied Physics Letters, Aug. 2014.
Gruber, et al., "Scanning confocal optical microscopy and magnetic resonance on single defect centers," Science, Jun. 1997.
Haeberle, et al., "Nanoscale nuclear magnetic imaging with chemical contrast," Nature Nanotechnology, Feb. 2015.
Haihua, et al., "Design of wideband anti-reflective sub wavelength nanostructures," Infrared and Laser Engineering, 2011.
Hall, et al., "Sensing of Fluctuating Nanoscale Magnetic Fields Using Nitrogen-Vacancy Centers in Diamond," Physical Review Letters, Nov. 2009.
Hanson, et al., "Coherent Dynamics of a single spin interacting with an adjustable spin bath," Sci. Am. Ass'n for the Advancement of Science, 2008.
Hanson, et al., "Polarization and Readout of Coupled Single Spins in Diamond," Physical Review Letters, 2006.
Hanson, et al., "Room-temperature manipulation and decoherence of a single spin in diamond," Physical Review, 2006.
Hanzawa, et al., "Zeeman effect on the zero-phonon line of the NV center in synthetic diamond," Physica B, Feb. 1993.

(56) References Cited

OTHER PUBLICATIONS

Hegyi & Yablonovitch, "Molecular imaging by optically detected electron spin resonance of nitrogen-vacancies in nanodiamonds," Nano Letters, Mar. 2013.
Hegyi & Yablonovitch, "Nanodiamond molecular imaging with enhanced contrast and expanded field of view," Journal of Biomedical Optics, Jan. 2014.
Hilser, et al., "All-optical control of the spin state in the NV-center in diamond," Physical Review B, Sep. 2012.
Hobbs, "Study of the Environmental and Optical Durability of AR Microstructures in Sapphire, ALON, and Diamond," Proceedings of SPIE, 2009.
Huebener, et al., "ODMR of NV centers in nano-diamonds covered with N@C60," Physica Status Solidi B, Oct. 2008.
Huxter, et al., "Vibrational and electronic dynamics of nitrogen-vacancy centres in diamond revealed by two-dimensional ultrafast spectroscopy," Nature Physics, Nov. 2013.
Ivady, et al., "Pressure and temperature dependence of the zero-field splitting in the ground state of NV centers in diamond: A first-principles study," Physical Review B, Dec. 2014.
Jarmola, et al., "Temperature- and Magnetic-Field-Dependent Longitudinal Spin Relaxation in Nitrogen-Vacancy Ensembles in Diamond," Physical Review Letters, May 2012.
Jensen, et al., "Light narrowing of magnetic resonances in ensembles of nitrogen-vacancy centers in diamond," Physical Review, Jan. 2013.
Kailath, "Linear Systems," Prentice Hall, 1979.
Karlsson, et al., "Diamond micro-optics: microlenses and antireflection structures surfaces for the infrared spectral region," Optics Express, 2003.
Khan & Hemmer, "Noise limitation in nano-scale imaging," Proceedings of SPIE, Dec. 2005.
Kim, et al., "Electron spin resonance shift and linewidth broadening of nitrogen-vacancy centers in diamond as a function of electron irradiation dose," Applied Physics Letters, Aug. 2012.
Kim, et al., "Magnetospectroscopy of acceptors in 'blue' diamonds," Physica B, Aug. 2001.
Kim, et al., "Zeeman effect of electronic Raman lines of accepters in elemental semiconductors: Boron in blue diamond," Physical Review B, Sep. 2000.
King, et al., "Optical polarization of 13C nuclei in diamond through nitrogen vacancy centers," Physical Review B, Feb. 2010.
Kok, et al., "Materials Science: Qubits in the pink," Nature, 2006.
Konenko, et al., "Formation of antireflective surface structures on diamond films by laser patterning," Applied Physics A, 1999.
Kraus, et al., "Magnetic field and temperature sensing with atomic-scale spin defects in silicon carbide," Scientific Reports, Jul. 2014.
Lai, et al., "Influence of a static magnetic field on the photoluminescence of an ensemble of nitrogen-vacancy color centers in a diamond single-crystal," Applied Physics Letters, Sep. 2009.
Lai, et al., "Optically detected magnetic resonance of a single Nitrogen-Vacancy electronic spin in diamond nanocrystals," CLEO/EQEC, 2009.
Laraoui, et al., "Nitrogen-vacancy-assisted magnetometry of paramagnetic centers in an individual diamond nanocrystal," Nano Letters, Jul. 2012.
Lazariev, et al., "A nitrogen-vacancy spin based molecular structure microscope using multiplexed projection reconstruction," Scientific Reports, Sep. 2015.
Lee, et al., "Vector magnetometry based on S=3/2 electronic spins," Physical Review B, Sep. 2015.
Lesik, et al., "Preferential orientation of NV defects in CVD diamond films grown on (113)-oriented substrates," Diamond and Related Materials, Jun. 2015.
Levchenko, et al., "Inhomogeneous broadening of optically detected magnetic resonance of the ensembles of nitrogen-vacancy centers in diamond by interstitial carbon atoms," Applied Physics Letters, Mar. 2015.
Liu, et al., "Electron spin studies of nitrogen vacancy centers in nanodiamonds," Acta Physica Sinica, Aug. 2013.
Liu, et al., "Fiber-integrated diamond-based magnetometer," Applied Physics Letters, Sep. 2013.
MacLaurin, et al., "Nanoscale magnetometry through quantum control of nitrogen-vacancy centres in rotationally diffusing nanodiamonds," New Journal of Physics, Jan. 2013.
Macs, et al., "Diamond as a magnetic field calibration probe," Journal of Physics D: Applied Physics, Apr. 2004.
Maletinsky, et al., "A robust scanning diamond sensor for nanoscale imaging with single nitrogen-vacancy centres," Nature Nanotechnology, May 2012.
Mamin, et al., "Multipulse Double-Quantum Magnetometry with Near-Surface Nitrogen-Vacancy Centers," Physical Review Letters, Jul. 2014.
Mamin, et al., "Nanoscale Nuclear Magnetic Resonance with a Nitrogen-Vacancy Spin Sensor," Science, Feb. 2013.
Manson, et al., "GR transitions in diamond: magnetic field measurements," Journal of Physics C, Nov. 1980.
Matsuda, et al., "Development of a plastic diamond anvil cell for high pressure magneto-photoluminescence in pulsed high magnetic fields," International Journal of Modern Physics B, Nov. 2004.
Maze, et al., "Nanoscale magnetic sensing using spin qubits in diamond," Nature Physics, 2009.
Meijer, et al., "Generation of single color centers by focused nitrogen implantation," Applied Physics Letters, Dec. 2005.
Millot, et al., "High-field Zeeman and paschen-back effects at high pressure in oriented ruby," Physical Review B, Oct. 2008.
Moriyama, et al., "Importance of electron-electron interactions and Zeeman splitting in single-wall carbon nanotube quantum dots," Physica E, Feb. 2005.
Mrozek, et al., "Circularly polarized microwaves for magnetic resonance study in the GHz range: Application to nitrogen-vacancy in diamonds," Applied Physics Letters, Jul. 2015.
Nagl, et al., "Improving surface and defect center chemistry of fluorescent nanodiamonds for imaging purposes-a review," Analytical and Bioanalaytical Chemistry, Oct. 2015.
Neumann, et al., "Excited-state spectroscopy of single NV defects in diamond using optically detected magnetic resonance," New Journal of Physics, Jan. 2009.
Nizovtsev & Kilin, "Optically Detected Magnetic Resonance Spectra of the 14NV-13C Spin Systems in Diamond: Analytical Theory and Experiment," Doklady of the National Academy of Sciences of Belarus, 2013.
Nizovtsev, et al., "Modeling fluorescence of single nitrogen-vacancy defect centers in diamond," Physica B—Condensed Matter, Dec. 2001.
Nizovtsev, et al., "Theoretical study of hyperfine interactions and optically detected magnetic resonance spectra by simulation of the C-291(NV)H—(172) diamond cluster hosting nitrogen-vacancy center," New Journal of Physics, Aug. 2014.
Nowodzinski, et al., "Nitrogen-Vacancy centers in diamond for current imaging at the redistributive layer level of Integrated Circuits," Microelectronics Reliability, Aug. 2015.
Nusran, et al., "Optimizing phase-estimation algorithms for diamond spin magnetometry," Physical Review B, Jul. 2014.
Ohashi, et al., "Negatively Charged Nitrogen-Vacancy Centers in a 5 nm Thin C-12 Diamond Film," Nano Letters, Oct. 2013.
Plakhotnik, et al., "Super-Paramagnetic Particles Chemically Bound to Luminescent Diamond : Single Nanocrystals Probed with Optically Detected Magnetic Resonance," Journal of Physical Chemistry C, Aug. 2015.
Rabeau, et al., "Implantation of labelled single nitrogen vacancy centers in diamond using N-15," Applied Physics Letters, Jan. 2006.
Ranjbar, et al., "Many-electron states of nitrogen-vacancy centers in diamond and spin density calculations," Physical Review B, Oct. 2011.
Reynhardt, "Spin-lattice relaxation of spin-1/2 nuclei in solids containing diluted paramagnetic impurity centers. I. Zeeman polarization of nuclear spin system," Concepts in Magnetic Resonance Part A, Sep. 2003.
Rogers, et al., "Singlet levels of the NV(-)centre in diamond," New Journal of Physics, Jan. 2015.

(56) References Cited

OTHER PUBLICATIONS

Rondin, et al., "Magnetometry with nitrogen-vacancy defects in diamond," Reports on Progress in Physics, May 2014.

Rondin, et al., "Nanoscale magnetic field mapping with a single spin scanning probe magnetometer," Applied Physics Letters, Apr. 2012.

Sarkar, et al., "Magnetic properties of graphite oxide and reduced graphene oxide," Physica E, 2014.

Scheuer, et al., "Accelerated 2D magnetic resonance spectroscopy of single spins using matrix completion," Scientific Reports, Dec. 2015.

Schirhagl, et al., "Nitrogen-vacancy centers in diamond: Nanoscale sensors for physics and biology," Annual Review of Physical Chemistry, Jan. 2014.

Schoenfeld & Harneit, "Real time magnetic field sensing and imaging using a single spin in diamond," Physical Review Letters, Jan. 2011.

Sedov, et al., "Si-doped nano- and microcrystalline diamond films with controlled bright photoluminescence of silicon-vacancy color centers," Diamond and Related Materials, Jun. 2015.

Shames, et al., "Magnetic resonance tracking of fluorescent nanodiamond fabrication," Journal of Physics D: Applied Physics, Apr. 2015.

Simanovskaia, et al., "Sidebands in optically detected magnetic resonance signals of nitrogen vacancy centers in diamond," Physical Review B, Jun. 2013.

Sotoma, et al., "Effective production of fluorescent nanodiamonds containing negatively-charged nitrogen-vacancy centers by ion irradiation," Diamond and Related Materials, Oct. 2014.

Steiner, et al., "Universal enhancement of the optical readout fidelity of single electron spins at nitrogen-vacancy centers in diamond," Physical Review B, Jan. 2010.

Steinert, et al., "High sensitivity magnetic imaging using an array of spins in diamond," Review of Scientific Instruments, Apr. 2010.

Stepanov, et al., "High-frequency and high-field optically detected magnetic resonance of nitrogen-vacancy centers in diamond," Applied Physics Letters, Feb. 2015.

Sternschulte, et al., "Uniaxial stress and Zeeman splitting of the 1.681 eV optical center in a homoepitaxial CVD diamond film," Diamond and Related Materials, Sep. 1995.

Storteboom, et al., "Lifetime investigation of single nitrogen vacancy centres in nanodiamonds," Optics Express, May 2015.

Tahara, et al., "Quantifying selective alignment of ensemble nitrogen-vacancy centers in (111) diamond," Applied Physics Letters, Nov. 2015.

Taylor, et al., "High-sensitivity diamond magnetometer with nanoscale resolution," Nature Physics, Oct. 2008.

Terblanche, et al., "13C spin-lattice relaxation in natural diamond: Zeeman relaxation at 4.7 T and 300 K due to fixed paramagnetic nitrogen defects," Solid State Nuclear Magnetic Resonance, Aug. 2001.

Terblanche, et al., "13C spin-lattice relaxation in natural diamond: Zeeman relaxation in fields of 500 to 5000 G at 300 K due to fixed paramagnetic nitrogen defects," Solid State Nuclear Magnetic Resonance, May 2001.

Tetienne, et al., "Magnetic-field-dependent photodynamics of single NV defects in diamond: an application to qualitative all-optical magnetic imaging," New Journal of Physics, Oct. 2012.

Tong, et al., "A hybrid-system approach for W state and cluster state generation," Optics Communication 310: 166-172 (2014).

Uhlen, et al., "New Diamond Nanofabrication process for hard x-ray zone plates," J. Of Vacuum Science & Tech. B, 2011.

Vershovskii & Dmitriev, "Combined excitation of an optically detected magnetic resonance in nitrogen-vacancy centers in diamond for precision measurement of the components of a magnetic field vector," Technical Physics Letters, Nov. 2015.

Vershovskii & Dmitriev, "Micro-scale three-component quantum magnetometer based on nitrogen-vacancy color centers in diamond crystal," Technical Physics Letters, Apr. 2015.

Wang, et al., "Optimizing ultrasensitive single electron magnetometer based on nitrogen-vacancy center in diamond," Chinese Science Bulletin, Aug. 2013.

Webber, et al., "Ab initio thermodynamics calculation of the relative concentration of NV- and NV0 defects in diamond," Physical Review B, Jan. 2012.

Wolf, et al., "Subpicotesla Diamond Magnetometry," Physical Review X, Oct. 2015.

Wolfe, et al., "Off-resonant manipulation of spins in diamond via precessing magnetization of a proximal ferromagnet," Physical Review B, May 2014.

Xue & Liu, "Producing GHZ state of nitrogen-vacancy centers in cavity QED," Journal of Modern Optics, Mar. 2013.

Yang & Gu, "Novel calibration techniques for high pulsed-magnetic fields using luminescence caused by photo," Journal of Huazhong University of Science and Technology, Jun. 2007.

Yavkin, et al., "Defects in Nanodiamonds: Application of High-Frequency cw and Pulse EPR, ODMR," Applied Magnetic Resonance, Oct. 2014.

Yu, et al., "Bright fluorescent nanodiamonds: no photobleaching and low cytotoxicity," J. Am. Chem. Soc., 2005.

Zhang, et al., "Laser-polarization-dependent and magnetically controlled optical bistability in diamond nitrogen-vacancy centers," Physics Letters A, Nov. 2013.

Zhang, et al., "Laser-polarization-dependent spontaneous emission of the zero phonon line from single nitrogen-vacancy center in diamond," Chinese Physics B, Apr. 2014.

Zhang, et al., "Scalable quantum information transfer between nitrogen-vacancy-center ensembles," Annals of Physics, Apr. 2015.

Zhao, et al., "Atomic-scale magnetometry of distant nuclear spin clusters via nitrogen-vacancy spin in diamond," Nature Nanotechnology, Apr. 2011.

Berman, et al. "Measurement of single electron and nuclear spin states based on optically detected magnetic resonance," J. Physics: Conf. Series 38: 167-170 (2006).

International Search Report and Written Opinion of the International Searching Authority dated Mar. 24, 2016 in international application PCT/US2016/014336.

"'Diamond Sensors, Detectors, and Quantum Devices' in Patent Application Approval Process," Chemicals & Chemistry (Feb 28, 2014).

"Findings from University of Stuttgart in physics reported," Physics Week (Jul. 7, 2009).

"New Findings on Nitrogen from Ecole Normale Superieure Summarized (Magnetic imaging with an ensemble of nitrogen vacancy-centers in diamond)," Physics Week (Jul. 21, 2015).

"Patent Issued for Diamond Sensors, Detectors, and Quantum Devices (U.S. Pat. No. 9,249,526)," Journal of Engineering (Feb. 15, 2016).

"Researchers Submit Patent Application, 'Diamond Sensors, Detectors, and Quantum Devices', for Approval," Chemicals & Chemistry (Apr. 11, 2014).

Massachusetts Institute of Technology; "Wide-Field Imaging Using Nitrogen Vacancies" in Patent Application Approval Process, Physics Week (2015).

Maze et al., "Nanoscale magnetic sensing with an individual electronic spin in diamond," Nature Physics (2008).

Steinert et al., "High-sensitivity magnetic imaging using an array of spins in diamond," Rev. Sci. Inst. (2010).

International Search Report and Written Opinion of the International Searching Authority dated Apr. 11, 2016 in international application PCT/US2016/014376.

International Search Report and Written Opinion of the International Searching Authority dated Apr. 11, 2016 in international application PCT/US2016/014384.

International Search Report and Written Opinion of the International Searching Authority dated Apr. 11, 2016 in international application PCT/US2016/014388.

International Search Report and Written Opinion of the International Searching Authority dated Apr. 11, 2016 in international application PCT/US2016/014395.

(56) References Cited

OTHER PUBLICATIONS

International Search Report and Written Opinion of the International Searching Authority dated Mar. 24, 2016 in international application PCT/US2016/014392.
International Search Report and Written Opinion of the International Searching Authority dated Mar. 24, 2016 in international application PCT/US2016/014403.
International Search Report and Written Opinion of the International Searching Authority dated Mar. 24, 2016, in international application PCT/US2016/014297.
International Search Report and Written Opinion of the International Searching Authority dated Mar. 25, 2016 in international application PCT/US2016/014363.
International Search Report and Written Opinion of the International Searching Authority dated Mar. 25, 2016 in international application PCT/US2016/014389.
International Search Report and Written Opinion of the International Searching Authority dated Mar. 28, 2016 in international application PCT/US2016/014380.
International Search Report and Written Opinion of the International Searching Authority dated Mar. 28, 2016 in international application PCT/US2016/014394.
International Search Report and Written Opinion of the International Searching Authority dated Mar. 29, 2016 in international application PCT/US2016/014325.
International Search Report and Written Opinion of the International Searching Authority dated Mar. 29, 2016 in international application PCT/US2016/014328.
International Search Report and Written Opinion of the International Searching Authority dated Mar. 29, 2016 in international application PCT/US2016/014330.
International Search Report and Written Opinion of the International Searching Authority dated Mar. 29, 2016 in international application PCT/US2016/014385.
International Search Report and Written Opinion of the International Searching Authority dated Mar. 30, 2016 in international application PCT/US2016/014298.
International Search Report and Written Opinion of the International Searching Authority dated Mar. 31, 2016 in international application PCT/US2016/014375.
International Search Report and Written Opinion of the International Searching Authority dated Mar. 31, 2016 in international application PCT/US2016/014396.
Macquarie et al., "Mechanical spin control of nitrogen-vacancy centers in diamond," <://arxiv.org/pdf/1306.6356.pdf>.
Poole, "What is GMSK Modulation—Gaussian Minimum Shift Keying." Radio-Electronics. Apr. 3, 2015 (Apr. 2015), pp. 1 [online] https://web.archive.org/web/20150403045840/http://www.radio-electronics.com/info/rf-technology-design/pm-phase-modulation/what-is-gmsk-gaussian-minimum-shift-keyingtutorial.php.
Rondin et al., "Magnetometry with nitrogen-vacancy defects in diamond." May 22, 2014 (May 22, 2014), pp. 1 [online] http://arxiv.org/pdf/1311.5214.pdf.
Correction: Nizovtsev & Kilin, "Optically Detected Magnetic Resonance Spectra of the 14NV-13C Spin Systems in Diamond: Analytical Theory and Experiment," Doklady of the National Academy of Sciences of Belarus, 2013.
Correction: Terblanche, et al., "13C spin-lattice relaxation in natural diamond: Zeeman relaxation at 4.7 T and 300 K due to fixed paramagnetic nitrogen defects," Solid State Nuclear Magnetic Resonance, Aug. 2001.
Correction: Tong, et al., "A hybrid-system approach for W state and cluster state generation," Optics Communication 310: 166-172 (2014).
Correction: Yang & Gu, "Novel calibration techniques for high pulsed-magnetic fields using luminescence caused by photo," Journal of Huazhong University of Science and Technology, Jun. 2007.
Correction: Zhang, et al., "Laser-polarization-dependent spontaneous emission of the zero phonon line from single nitrogen-vacancy center in diamond," Chinese Physics B, Apr. 2014.

Acosta et al., "Broadband magnetometry by infrared-absorption detection of nitrogen-vacancy ensembles in diamond," Appl. Phys. Letters 97: 174104 (2010).
Barry et al., "Optical magnetic detection of single-neuron action potentials using quantum defects in diamond," submitted to Quantum Physics on Feb. 2, 2016.
Clevenson, et al., "Broadband magnetometry and temperature sensing with a light-trapping diamond waveguide," Nature Physics 11: 393-397 (May 2015).
Constable, "Geomagnetic Spectrum, Temporal." In Encyclopedia of Geomagnetism and Paleomagnetism, 353-355. Springer: Dordrecht, Netherlands (2007).
International Search Report and Written Opinion of the International Searching Authority dated Jun. 10, 2016 from related PCT application PCT/US2016/014290.
International Search Report and Written Opinion of the International Searching Authority dated Jun. 2, 2016, from related PCT application PCT/US2016/014386.
International Search Report and Written Opinion of the International Searching Authority dated Jun. 2, 2016, from related PCT application PCT/US2016/014387.
International Search Report and Written Opinion of the International Searching Authority dated Jun. 6, 2016, from related PCT application PCT/US2016/014291.
International Search Report and Written Opinion of the International Searching Authority dated Jun. 9, 2016 from related PCT application PCT/US2016/014333.
International Search Report and Written Opinion of the International Searching Authority dated May 26 2016, from related PCT application PCT/US2016/014331.
Le Sage et al., "Efficient photon detection from color centers in a diamond optical waveguide," Phys. Rev. B 85: 121202(R) (2012).
Nobauer et al., "Smooth optimal quantum control for robust solid state spin magnetometry," Retrieved from http://www.arxiv.org/abs/1412.5051 (Dec. 2014).
Polatomic. "AN/ASQ-233A Digital Magnetic Anomaly Detective Set" Retrieved May 9, 2016, from http://polatomic.com/images/DMAD_Data_Sheet_09-2009.pdf (2009).
Shao et al., "Diamond Color Center Based FM Microwave Demodulator," in Conference on Lasers and Electro-Optics, OSA Technical Digest (online) (Optical Society of America, 2016), paper JTh2A.136.
US Notice of Allowance dated Apr. 20, 2016, on U.S. Appl. No. 15/003,718.
US Office Action dated May 13, 2016, from related patent U.S. Appl. No. 14/676,740.
US Office Action dated May 6, 2016, from related patent U.S. Appl. No. 14/659,498.
Wahlstrom et al., "Modeling Magnetic Fields Using Gaussian Processes," 2013 IEEE International Conference on Acoustics, Speech, and Signal Processing, pp. 3522-3526 (May 26-31, 2013).
Fallah et al., "Multi-sensor approach in vessel magnetic wake imaging," Wave Motion 51(1): 60-76 (Jan. 2014), retrieved from http://www.sciencedirect.com/science/article/pii/S0165200113 (Aug. 21, 2016).
International Search Report and Written opinion of the International Searching Authority dated Jul. 12, 2016, from related PCT application PCT/US2016/014287, 14 pages.
International Search Report and Written Opinion of the International Searching Authority dated Sep. 13, 2016, from related PCT application PCT/US16/14377, 11 pages.
Notice of Allowance dated Sep. 8, 2016, from related U.S. Appl. No. 15/003,298, 10 pages.
Teale, "Magnetometry with Ensembles of Nitrogen Vacancy Centers in Bulk Diamond," Master's Thesis, Massachusetts Institute of Technology Department of Electrical Engineering and Computer Science (Sep. 2015), 57 pages.
US Office Action dated Jul. 29, 2016 from related U.S. Appl. No. 14/680,877, 8 pages.
Notice of Allowance dated Aucust 17, 2016, from U.S. Appl. No. 15/003,718, 8 pages.

(56) References Cited

OTHER PUBLICATIONS

Soykal et al., "Quantum metrology with a single spin-3/2 defect in silicon carbide," Mesoscale and Nanoscale Physics (May 24, 2016), 9 pages.
US Office Action dated Aug. 24, 2016 from related U.S. Appl. No. 14/676,740, 19 pages.
US Office Action dated Oct. 14, 2016 from related U.S. Appl. No. 15/003,677, 13 pages.
Widmann et al., "Coherent control of single spins in silicon carbide at room temperature," Nature Materials, 12: 164-168 (2015) (available online Dec. 1, 2014).
International Preliminary Report on Patentability dated Oct. 20, 2016 from related PCT application PCT/US2015/024723, 7 pages.
US Office Action dated Nov. 2, 2016, from related U.S. Appl. No. 15/003,256, 19 pages.
US Office Action dated Nov. 3, 2016, from related U.S. Appl. No. 15/204,675, 9 pages.
US Office Action dated Oct. 19, 2016, from related U.S. Appl. No. 15/218,821, 6 pages.

\* cited by examiner

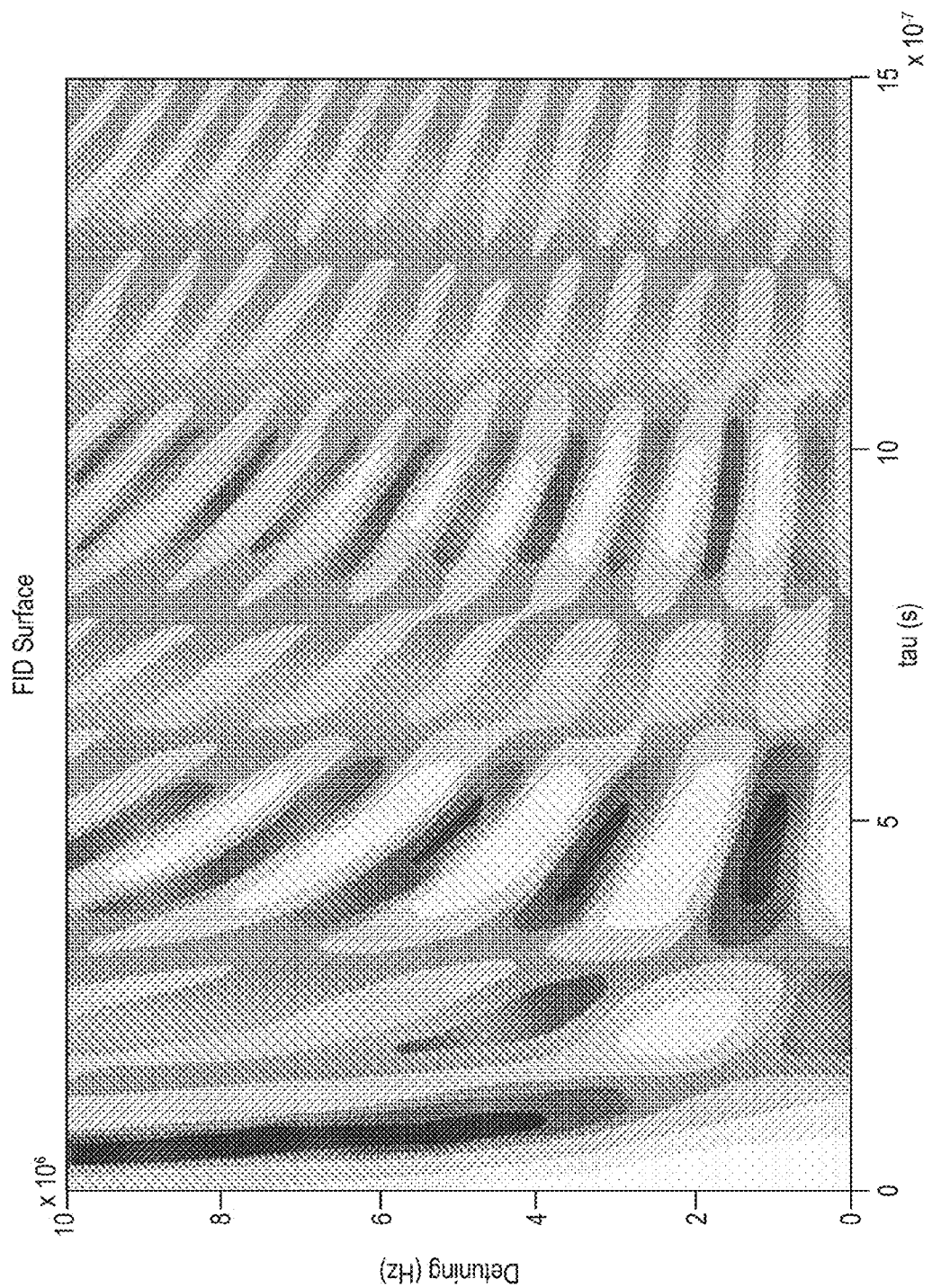

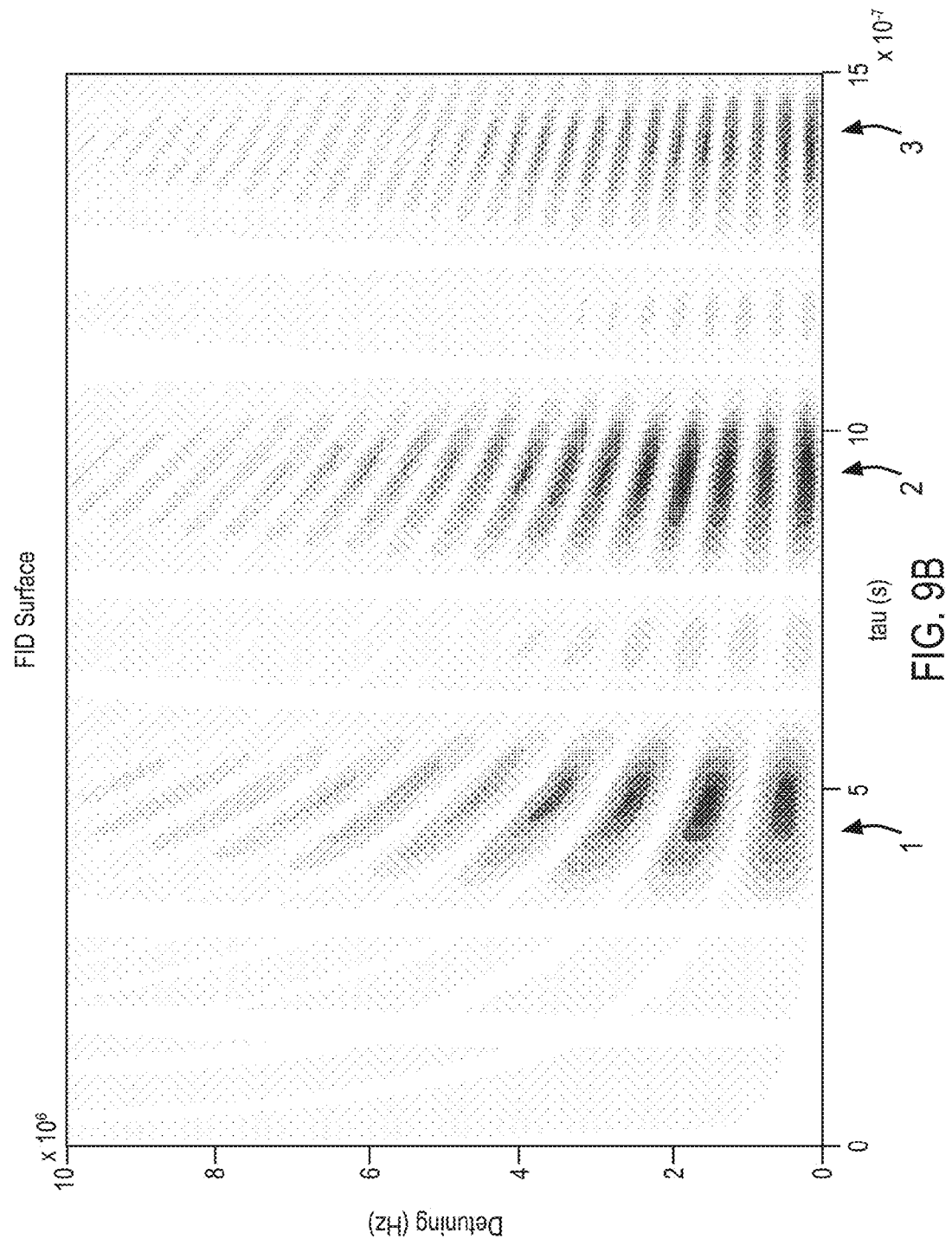

APPARATUS AND METHOD FOR HIGH SENSITIVITY MAGNETOMETRY MEASUREMENT AND SIGNAL PROCESSING IN A MAGNETIC DETECTION SYSTEM

CROSS-REFERENCE TO RELATED PATENT APPLICATION

This application claims the benefit of priority to U.S. Patent Application No. 62/107,289, filed Jan. 23, 2015, the entire contents of which are incorporated by reference herein in its entirety.

FIELD

The present disclosure generally relates to magnetic detection systems, and more particularly, to measurement and signal processing methods for a magnetic detection system.

BACKGROUND

A number of industrial applications including, but not limited to, medical devices, communication devices, and navigation systems, as well as scientific areas such as physics and chemistry can benefit from magnetic detection and imaging. Many advanced magnetic imaging systems can operate in limited conditions, for example, high vacuum and/or cryogenic temperatures, which can make them inapplicable for imaging applications that require ambient conditions. Furthermore, small size, weight and power (SWAP) magnetic sensors of moderate sensitivity, vector accuracy, and bandwidth are valuable in many applications.

Atomic-sized nitrogen-vacancy (NV) centers in diamond have been shown to have excellent sensitivity for magnetic field measurement and enable fabrication of small magnetic sensors that can readily replace existing-technology (e.g., Hall-effect) systems and devices. The sensing capabilities of diamond NV (DNV) sensors are maintained at room temperature and atmospheric pressure, and these sensors can be even used in liquid environments (e.g., for biological imaging). DNV sensing allows measurement of 3-D vector magnetic fields that is beneficial across a very broad range of applications, including communications, geological sensing, navigation, and attitude determination.

SUMMARY

According to certain embodiments, a system for magnetic detection may include a nitrogen vacancy (NV) diamond material comprising a plurality of NV centers, a radio frequency (RF) excitation source configured to provide RF excitation to the NV diamond material, an optical excitation source configured to provide optical excitation to the NV diamond material, an optical detector configured to receive an optical signal emitted by the NV diamond material, a magnetic field generator configured to generate a magnetic field applied to the NV diamond material, and a controller. The controller may be configured to control the optical excitation source and the RF excitation source to apply a first pulse sequence comprising two optical excitation pulses and two RF excitation pulses to the NV diamond material, receive a first light detection signal from the optical detector based on an optical signal emitted by the NV diamond material due to the first pulse sequence, measure a first value of the first light detection signal at a first reference period, the first reference period being before a period of the first light detection signal associated with the two RF excitation pulses of the first pulse sequence provided to the NV diamond material, measure a second value of the first light detection signal at a second reference period, the second reference period being after the period of the first light detection signal associated with the two RF excitation pulses of the first pulse sequence provided to the NV diamond material, compute a first measurement based on the measured first and second values of the first light detection signal, control the optical excitation source and the RF excitation source to apply a second pulse sequence comprising two optical excitation pulses and two RF excitation pulses to the NV diamond material, receive a second light detection signal from the optical detector based on an optical signal emitted by the NV diamond material due to the second pulse sequence, measure a first value of the second light detection signal at a first reference period, the first reference period being before a period of the second light detection signal associated with the two RF excitation pulses of the second pulse sequence provided to the NV diamond material, measure a second value of the second light detection signal at a second reference period, the second reference period being after the period of the second light detection signal associated with the two RF excitation pulses of the second pulse sequence provided to the NV diamond material, and compute a second measurement based on the measured first and second values of the second light detection signal. The first measurement may be based on a high resonance frequency of the NV diamond material, and the second measurement may be based on a low resonance frequency of the NV diamond material.

According to one aspect, a high resonance frequency and a low resonance frequency may be resonance frequencies associated with an axis of an NV center of the NV diamond material.

According to one aspect, a controller may be further configured to compute a change in an external magnetic field acting on the NV diamond material based on the first and second measurements.

According to other embodiments, a system for magnetic detection may include a nitrogen vacancy (NV) diamond material comprising a plurality of NV centers, a radio frequency (RF) excitation source configured to provide RF excitation to the NV diamond material, an optical excitation source configured to provide optical excitation to the NV diamond material, an optical detector configured to receive an optical signal emitted by the NV diamond material, a magnetic field generator configured to generate a magnetic field applied to the NV diamond material, and a controller. The controller may be configured to control the optical excitation source and the RF excitation source to apply a pulse sequence comprising two optical excitation pulses and two RF excitation pulses to the NV diamond material, receive a light detection signal from the optical detector based on an optical signal emitted by the NV diamond material due to the pulse sequence, measure a first value of the light detection signal at a first reference period, the first reference period being before a period of the light detection signal associated with the two RF excitation pulses provided to the NV diamond material, measure a second value of the light detection signal at a second reference period, the second reference period being after the period of the light detection signal associated with the two RF excitation pulses provided to the NV diamond material, and compute a measurement signal based on the measured first and second values.

According to one aspect, a controller may be further configured to measure the first value and the second value based on an average of values of the light detection signal within the first reference period and the second reference period.

According to one aspect, a controller may be further configured to compute the measurement signal based on the average of the first value and the second value.

According to one aspect, a controller may be further configured to measure a third value of the light detection signal at a signal period, the signal period being after the first reference period and before the second reference period.

According to one aspect, a controller may be further configured to compute the measurement signal based on a difference between the average of the first and second values and the third value.

According to one aspect, a first reference period may be associated with one of the two optical excitation pulses and a second reference period may be associated with the other of the two optical excitation pulses.

According to other embodiments, a system for magnetic detection may include a nitrogen vacancy (NV) diamond material comprising a plurality of NV centers, a radio frequency (RF) excitation source configured to provide RF excitation to the NV diamond material, an optical excitation source configured to provide optical excitation to the NV diamond material, an optical detector configured to receive an optical signal emitted by the NV diamond material, a magnetic field generator configured to generate a magnetic field applied to the NV diamond material, and a controller. The controller may be configured to control the optical excitation source and the RF excitation source to apply a first pulse sequence comprising two optical excitation pulses and two RF excitation pulses to the NV diamond material, receive a first light detection signal from the optical detector based on an optical signal emitted by the NV diamond material due to the first pulse sequence, compute a first measurement based on the first light detection signal, control the optical excitation source and the RF excitation source to apply a second pulse sequence comprising two optical excitation pulses and two RF excitation pulses to the NV diamond material, receive a second light detection signal from the optical detector based on an optical signal emitted by the NV diamond material due to the second pulse sequence, and compute a second measurement based on the second light detection signal. The first measurement may be based on a high resonance frequency of the NV diamond material, and the second measurement may be based on a low resonance frequency of the NV diamond material.

According to one aspect, a high resonance frequency and a low resonance frequency may be resonance frequencies associated with an axis of an NV center of the NV diamond material.

According to one aspect, two RF excitation pulses of the first pulse sequence may be applied at a frequency detuned from the high resonance frequency of the NV diamond material.

According to one aspect, two RF excitation pulses of the second pulse sequence may be applied at a frequency detuned from the low resonance frequency of the NV diamond material.

According to one aspect, a controller may be further configured to compute a change in an external magnetic field acting on the NV diamond material based on the first and second measurements.

According to other embodiments, a system for magnetic detection may include a nitrogen vacancy (NV) diamond material comprising a plurality of NV centers, a radio frequency (RF) excitation source configured to provide RF excitation to the NV diamond material, an optical excitation source configured to provide optical excitation to the NV diamond material, an optical detector configured to receive an optical signal emitted by the NV diamond material, a magnetic field generator configured to generate a magnetic field applied to the NV diamond material, and a controller. The controller may be configured to control the optical excitation source and the RF excitation source to apply a plurality of pulse sequences to the NV diamond material, each of the plurality of pulse sequences comprising two optical excitation pulses and an RF excitation pulse, wherein a time period of application of the RF excitation pulse may be varied among each of the plurality of pulse sequences. The controller may be further configured to receive a plurality of light detection signals from the optical detector based on an optical signal emitted by the NV diamond material due to the plurality of pulse sequences, measure a first value of each of the plurality of light detection signals at a first reference period, the first reference period being before a period associated with the RF excitation pulse of each of the plurality of pulse sequences, measure a second value of each of the plurality of light detection signals at a second reference period, the second reference period being after the period associated with the RF excitation pulse of each of the plurality of pulse sequences, compute a plurality of measurement signals based on the plurality of measured first and second values, and calculate a frequency of the plurality of measurement signals.

According to one aspect, a frequency may be a resonant Rabi frequency.

According to one aspect, an RF excitation source may be a microwave antenna.

According to one aspect, a microwave antenna may be a small loop antenna.

According to one aspect, a small loop antenna may comprise a loop having a diameter of about 2 mm.

According to one aspect, a microwave antenna may be configured to provide a microwave power of at least 10 watts.

According to one aspect, a controller may be configured to apply one of the two optical excitation pulses, followed by the RF excitation pulse, and followed by the other of the two optical excitation pulses during each of the plurality of pulse sequences.

According to one aspect, a controller may be configured to apply a window between the one of the two optical excitation pulses and the RF excitation pulse during each of the plurality of pulse sequences, the window being a time period in which no excitation or optical excitation is applied to the NV diamond material.

According to one aspect, a controller may be further configured to identify a first minimum of the plurality of measurement signals.

According to other embodiments, a system for magnetic detection may include a nitrogen vacancy (NV) diamond material comprising a plurality of NV centers, a radio frequency (RF) excitation source configured to provide RF excitation to the NV diamond material, an optical excitation source configured to provide optical excitation to the NV diamond material, an optical detector configured to receive an optical signal emitted by the NV diamond material, a magnetic field generator configured to generate a magnetic field applied to the NV diamond material, and a controller. The controller may be configured to control the optical excitation source and the RF excitation source to apply a plurality of pulse sequences to the NV diamond material, each of the plurality of pulse sequences comprising two optical excitation pulses and two RF excitation pulses, wherein a time period between application of the two RF excitation pulses is varied among each of the plurality of pulse sequences, receive a plurality of light detection signals from the optical detector based on an optical signal emitted by the NV diamond material due to the plurality of pulse sequences, measure a first value of each of the plurality of light detection signals at a first reference period, the first reference period being before a period associated with the RF excitation pulse of each of the plurality of pulse sequences, measure a second value of each of the plurality of light detection signals at a second reference period, the second reference period being after the period associated with the RF excitation pulse of each of the plurality of pulse sequences, compute a plurality of measurement signals based on the plurality of measured first and second values, and calculate a decay time of the plurality of measurement signals.

According to one aspect, two RF excitation pulses of each of the plurality of pulse sequences may be applied at a frequency of about 10 MHz.

According to other embodiments, a system for magnetic detection having a nitrogen vacancy (NV) diamond material comprising a plurality of NV centers may include means for providing RF excitation to the NV diamond material, means for providing optical excitation to the NV diamond material, means for receiving an optical signal emitted by the NV diamond material, means for generating a magnetic field applied to the NV diamond material, means for applying a pulse sequence comprising two optical excitation pulses and two RF excitation pulses to the NV diamond material, means for receiving a light detection signal based on an optical signal emitted by the NV diamond material due to the pulse sequence, means for measuring a first value of the light detection signal at a first reference period, the first reference period being before a period of the light detection signal associated with the two RF excitation pulses provided to the NV diamond material, means for measuring a second value of the light detection signal at a second reference period, the second reference period being after the period of the light detection signal associated with the two RF excitation pulses provided to the NV diamond material, and means for computing a measurement signal based on the measured first and second values.

According to other embodiments, a method for detecting a magnetic field acting on a nitrogen vacancy (NV) diamond material comprising a plurality of NV centers may include controlling an optical excitation source and an RF excitation source to apply a pulse sequence comprising two optical excitation pulses and two RF excitation pulses to the NV diamond material, receiving a light detection signal from an optical detector based on an optical signal emitted by the NV diamond material due to the pulse sequence, measuring a first value of the light detection signal at a first reference period, the first reference period being before a period of the light detection signal associated with the two RF excitation pulses provided to the NV diamond material, measuring a second value of the light detection signal at a second reference period, the second reference period being after the period of the light detection signal associated with the two RF excitation pulses provided to the NV diamond material, and computing a measurement signal based on the measured first and second values.

According to one aspect, a method may further comprise computing the measurement signal based on the average of the first value and the second value.

According to one aspect, a method may further comprise measuring a third value of the light detection signal at a signal period, the signal period being after the first reference period and before the second reference period.

According to one aspect, a method may further comprise computing the measurement signal based on a difference between the average of the first and second values and the third value.

According to other embodiments, a system for magnetic detection may include a magneto-defect center material comprising a plurality of magneto-defect centers, a radio frequency (RF) excitation source configured to provide RF excitation to the magneto-defect center material, an optical excitation source configured to provide optical excitation to the magneto-defect center material, an optical detector configured to receive an optical signal emitted by the magneto-defect center material, a magnetic field generator configured to generate a magnetic field applied to the magneto-defect center material, and a controller. The controller may be configured to control the optical excitation source and the RF excitation source to apply a pulse sequence comprising two optical excitation pulses and two RF excitation pulses to the magneto-defect center material, receive a light detection signal from the optical detector based on an optical signal emitted by the magneto-defect center material due to the pulse sequence, measure a first value of the light detection signal at a first reference period, the first reference period being before a period of the light detection signal associated with the two RF excitation pulses provided to the magneto-defect center material, measure a second value of the light detection signal at a second reference period, the second reference period being after the period of the light detection signal associated with the two RF excitation pulses provided to the magneto-defect center material, and compute a measurement signal based on the measured first and second values.

According to other embodiments, a system for magnetic detection having a nitrogen vacancy (NV) diamond material comprising a plurality of NV centers may include means for providing RF excitation to the NV diamond material, means for providing optical excitation to the NV diamond material, means for receiving an optical signal emitted by the NV diamond material, means for generating a magnetic field applied to the NV diamond material, and means for applying a first pulse sequence comprising two optical excitation pulses and two RF excitation pulses to the NV diamond material, means for receiving a first light detection signal based on an optical signal emitted by the NV diamond material due to the first pulse sequence, means for computing a first measurement based on the first light detection signal, means for applying a second pulse sequence comprising two optical excitation pulses and two RF excitation pulses to the NV diamond material, means for receiving a second light detection signal based on an optical signal emitted by the NV diamond material due to the second pulse sequence, and means for computing a second measurement based on the second light detection signal. The first measurement may be based on a high resonance frequency of the NV diamond material, and the second measurement may be based on a low resonance frequency of the NV diamond material.

According to other embodiments, a method for detecting a magnetic field acting on a nitrogen vacancy (NV) diamond material comprising a plurality of NV centers may include controlling an optical excitation source and an RF excitation source to apply a first pulse sequence comprising two optical excitation pulses and two RF excitation pulses to the NV diamond material, receiving a first light detection signal from the optical detector based on an optical signal emitted by the NV diamond material due to the first pulse sequence, computing a first measurement based on the first detection signal, controlling the optical excitation source and the RF excitation source to apply a second pulse sequence comprising two optical excitation pulses and two RF excitation pulses to the NV diamond material, receiving a second light detection signal from the optical detector based on an optical signal emitted by the NV diamond material due to the second pulse sequence, and computing a second measurement based on the second light detection signal. The first measurement may be based on a high resonance frequency of the NV diamond material, and the second measurement may be based on a low resonance frequency of the NV diamond material.

According to one aspect, a high resonance frequency and a low resonance frequency may be resonance frequencies associated with an axis of an NV center of the NV diamond material.

According to one aspect, a method may further comprise computing a change in an external magnetic field acting on the NV diamond material based on the first and second measurements.

According to other embodiments, a system for magnetic detection may include a magneto-defect center material comprising a plurality of magneto-defect centers, a radio frequency (RF) excitation source configured to provide RF excitation to the magneto-defect center material, an optical excitation source configured to provide optical excitation to the magneto-defect center material, an optical detector configured to receive an optical signal emitted by the magneto-defect center material, a magnetic field generator configured to generate a magnetic field applied to the magneto-defect center material, and a controller. The controller may be configured to control the optical excitation source and the RF excitation source to apply a first pulse sequence comprising two optical excitation pulses and two RF excitation pulses to the magneto-defect center material, receive a first light detection signal from the optical detector based on an optical signal emitted by the magneto-defect center material due to the first pulse sequence, compute a first measurement based on the first detection signal, control the optical excitation source and the RF excitation source to apply a second pulse sequence comprising two optical excitation pulses and two RF excitation pulses to the magneto-defect center material, receive a second light detection signal from the optical detector based on an optical signal emitted by the magneto-defect center material due to the second pulse sequence, and compute a second measurement based on the second light detection signal. The first measurement may be based on a high resonance frequency of the magneto-defect center material, and the second measurement may be based on a low resonance frequency of the magneto-defect center material.

BRIEF DESCRIPTION OF THE DRAWINGS

FIG. 9A is a free induction decay surface plot where both the free precession time $\tau$ and the RF detuning frequency $\Delta$ are varied using the Ramsey sequence of FIG. 7.
FIG. 9B is a plot showing a gradient of the free induction decay surface plot of FIG. 9B.

DETAILED DESCRIPTION

The present disclosure relates to apparatuses and methods for stimulating a NV diamond in a magnetic detection system using an optimized stimulation process to significantly increase magnetic sensitivity of the detection system. The system utilizes a Ramsey pulse sequence to detect and measure the magnetic field acting on the system. Parameters relating to the Ramsey pulse sequence are optimized before measurement of the magnetic field. These parameters include the resonant Rabi frequency, the free precession time (tau), and the detuning frequency, all of which help improve the sensitivity of the measurement. These parameters may be optimally determined using calibration tests utilizing other optical detection techniques, such as a Rabi pulse sequence or additional Ramsey sequences. In addition, parameters, in particular the resonant Rabi frequency, may be further optimized by an increase in power of the RF excitation source, which may be achieved through the use of a small loop antenna. During measurement of the magnetic field, the RF excitation pulses applied during the Ramsey sequences may be set to occur at separate resonance frequencies associated with different spin states (e.g., $m_s=+1$ or $m_s=-1$). By utilizing separate resonance locations, changes due to temperature and/or strain effects in the system and changes due to the external magnetic field may be separated out, thus improving the accuracy of the measurements. Finally, processing of the data obtained during measurement is further optimized by the use of at least two reference windows, the average of which is used to obtain the signal. The above provide a magnetic detection system capable of improved sensitivity in detection of a magnetic field. In some embodiments, the optimized measurement process may result in a sensitivity of the magnetic detection system of about 9 nT/√Hz or less.

The NV Center, its Electronic Structure, and Optical and RF Interaction

Figure 1:
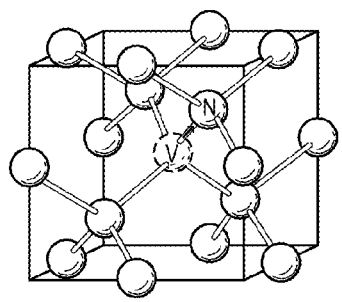
FIG. 1 illustrates one orientation of an NV center in a diamond lattice.

The NV center in a diamond comprises a substitutional nitrogen atom in a lattice site adjacent a carbon vacancy as shown in FIG. 1. The NV center may have four orientations, each corresponding to a different crystallographic orientation of the diamond lattice.

The NV center may exist in a neutral charge state or a negative charge state. Conventionally, the neutral charge state uses the nomenclature $NV^0$, while the negative charge state uses the nomenclature NV, which is adopted in this description.

The NV center has a number of electrons, including three unpaired electrons, each one from the vacancy to a respective of the three carbon atoms adjacent to the vacancy, and a pair of electrons between the nitrogen and the vacancy. The NV center, which is in the negatively charged state, also includes an extra electron.

Figure 2:
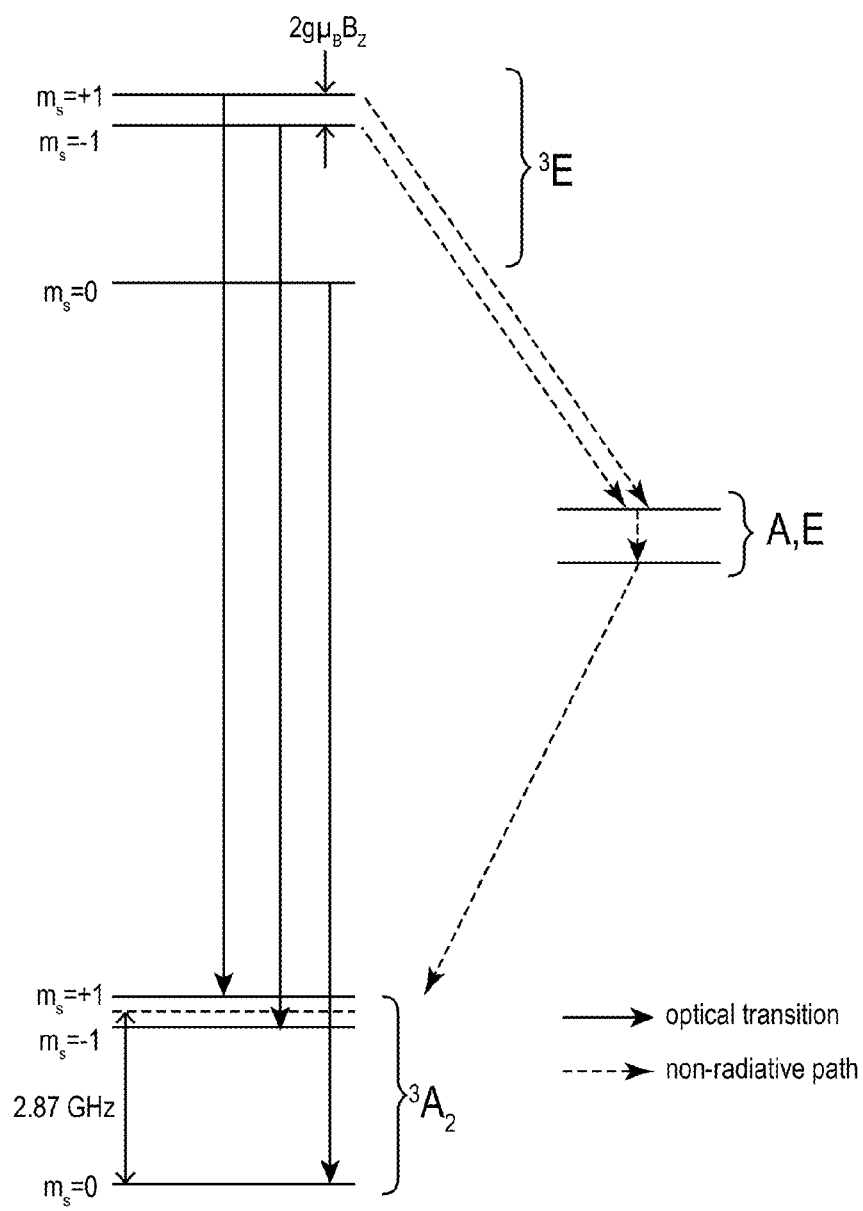
FIG. 2 is an energy level diagram showing energy levels of spin states for the NV center.

The NV center has rotational symmetry, and as shown in FIG. 2, has a ground state, which is a spin triplet with $^3A_2$ symmetry with one spin state $m_s=0$, and two further spin states $m_s=+1$, and $m_s=-1$. In the absence of an external magnetic field, the $m_s=\pm1$ energy levels are offset from the $m_s=0$ due to spin-spin interactions, and the $m_s=\pm1$ energy levels are degenerate, i.e., they have the same energy. The $m_s=0$ spin state energy level is split from the $m_s=\pm1$ energy levels by an energy of 2.87 GHz for a zero external magnetic field.

Introducing an external magnetic field with a component along the NV axis lifts the degeneracy of the $m_s=\pm1$ energy levels, splitting the energy levels $m_s=\pm1$ by an amount $2g\mu_B Bz$, where g is the g-factor, $\mu_B$ is the Bohr magneton, and Bz is the component of the external magnetic field along the NV axis. This relationship is correct to a first order and inclusion of higher order corrections is a straightforward matter and will not affect the computational and logic steps in the systems and methods described below.

The NV center electronic structure further includes an excited triplet state $^3E$ with corresponding $m_s=0$ and $m_s=\pm1$ spin states. The optical transitions between the ground state $^3A_2$ and the excited triplet $^3E$ are predominantly spin conserving, meaning that the optical transitions are between initial and final states that have the same spin. For a direct transition between the excited triplet $^3E$ and the ground state $^3A_2$, a photon of red light is emitted with a photon energy corresponding to the energy difference between the energy levels of the transitions.

There is, however, an alternative non-radiative decay route from the triplet $^3E$ to the ground state $^3A_2$ via intermediate electron states, which are thought to be intermediate singlet states A, E with intermediate energy levels. Significantly, the transition rate from the $m_s=\pm1$ spin states of the excited triplet $^3E$ to the intermediate energy levels is significantly greater than the transition rate from the $m_s=0$ spin state of the excited triplet $^3E$ to the intermediate energy levels. The transition from the singlet states A, E to the ground state triplet $^3A_2$ predominantly decays to the $m_s=0$ spin state over the $m_s=\pm1$ spins states. These features of the decay from the excited triplet $^3E$ state via the intermediate singlet states A, E to the ground state triplet $^3A_2$ allows that if optical excitation is provided to the system, the optical excitation will eventually pump the NV center into the $m_s=0$ spin state of the ground state $^3A_2$. In this way, the population of the $m_s=0$ spin state of the ground state $^3A_2$ may be "reset" to a maximum polarization determined by the decay rates from the triplet $^3E$ to the intermediate singlet states.

Another feature of the decay is that the fluorescence intensity due to optically stimulating the excited triplet $^3E$ state is less for the $m_s=\pm1$ states than for the $m_s=0$ spin state. This is so because the decay via the intermediate states does not result in a photon emitted in the fluorescence band, and because of the greater probability that the $m_s=\pm1$ states of the excited triplet $^3E$ state will decay via the non-radiative decay path. The lower fluorescence intensity for the $m_s=\pm1$ states than for the $m_s=0$ spin state allows the fluorescence intensity to be used to determine the spin state. As the population of the $m_s=\pm1$ states increases relative to the $m_s=0$ spin, the overall fluorescence intensity will be reduced.

The NV Center, or Magneto-Optical Defect Center, Magnetic Sensor System

Figure 3:
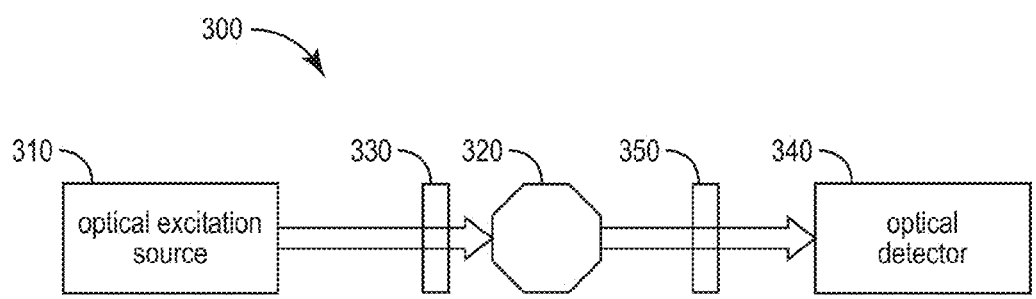
FIG. 3 is a schematic diagram illustrating a conventional NV center magnetic sensor system.

FIG. 3 is a schematic diagram illustrating a conventional NV center magnetic sensor system 300 that uses fluorescence intensity to distinguish the $m_s=\pm1$ states, and to measure the magnetic field based on the energy difference between the $m_s=+1$ state and the $m_s=-1$ state. The system 300 includes an optical excitation source 310, which directs optical excitation to an NV diamond material 320 with NV centers. The system further includes an RF excitation source 330, which provides RF radiation to the NV diamond material 320. Light from the NV diamond may be directed through an optical filter 350 to an optical detector 340.

The RF excitation source 330 may be a microwave coil, for example. The RF excitation source 330, when emitting RF radiation with a photon energy resonant with the transition energy between ground $m_s=0$ spin state and the $m_s=+1$ spin state, excites a transition between those spin states. For such a resonance, the spin state cycles between ground $m_s=0$ spin state and the $m_s=+1$ spin state, reducing the population in the $m_s=0$ spin state and reducing the overall fluorescence at resonances. Similarly, resonance occurs between the $m_s=0$ spin state and the $m_s=-1$ spin state of the ground state when the photon energy of the RF radiation emitted by the RF excitation source is the difference in energies of the $m_s=0$ spin state and the $m_s=-1$ spin state, or between the $m_s=0$ spin state and the $m_s=+1$ spin state, there is a decrease in the fluorescence intensity.

The optical excitation source 310 may be a laser or a light emitting diode, for example, which emits light in the green, for example. The optical excitation source 310 induces fluorescence in the red, which corresponds to an electronic transition from the excited state to the ground state. Light from the NV diamond material 320 is directed through the optical filter 350 to filter out light in the excitation band (in the green, for example), and to pass light in the red fluorescence band, which in turn is detected by the detector 340. The optical excitation light source 310, in addition to exciting fluorescence in the diamond material 320, also serves to reset the population of the $m_s=0$ spin state of the ground state $^3A_2$ to a maximum polarization, or other desired polarization.

Figure 4:
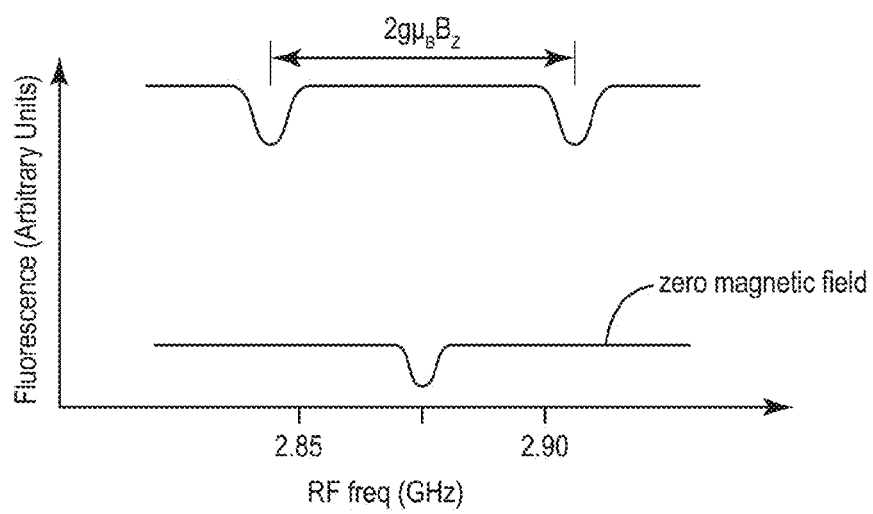
FIG. 4 is a graph illustrating the fluorescence as a function of an applied RF frequency of an NV center along a given direction for a zero magnetic field.

For continuous wave excitation, the optical excitation source 310 continuously pumps the NV centers, and the RF excitation source 330 sweeps across a frequency range that includes the zero splitting (when the $m_s=\pm1$ spin states have the same energy) photon energy of 2.87 GHz. The fluorescence for an RF sweep corresponding to a diamond material 320 with NV centers aligned along a single direction is shown in FIG. 4 for different magnetic field components Bz along the NV axis, where the energy splitting between the $m_s=-1$ spin state and the $m_s=+1$ spin state increases with Bz. Thus, the component Bz may be determined. Optical excitation schemes other than continuous wave excitation are contemplated, such as excitation schemes involving pulsed optical excitation, and pulsed RF excitation. Examples of pulsed excitation schemes include Ramsey pulse sequence (described in more detail below), and spin echo pulse sequence.

Figure 5:
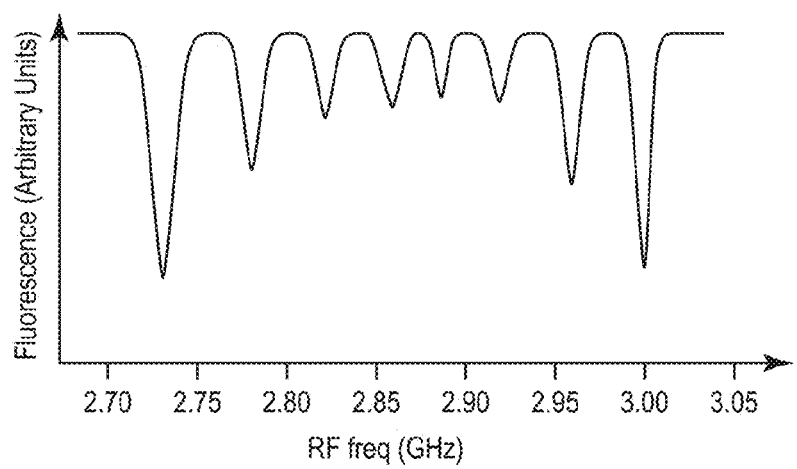
FIG. 5 is a graph illustrating the fluorescence as a function of an applied RF frequency for four different NV center orientations for a non-zero magnetic field.

In general, the diamond material 320 will have NV centers aligned along directions of four different orientation classes. FIG. 5 illustrates fluorescence as a function of RF frequency for the case where the diamond material 320 has NV centers aligned along directions of four different orientation classes. In this case, the component Bz along each of the different orientations may be determined. These results, along with the known orientation of crystallographic planes of a diamond lattice, allow not only the magnitude of the external magnetic field to be determined, but also the direction of the magnetic field.

While FIG. 3 illustrates an NV center magnetic sensor system 300 with NV diamond material 320 with a plurality of NV centers, in general, the magnetic sensor system may instead employ a different magneto-optical defect center material, with a plurality of magneto-optical defect centers. The electronic spin state energies of the magneto-optical defect centers shift with magnetic field, and the optical response, such as fluorescence, for the different spin states is not the same for all of the different spin states. In this way, the magnetic field may be determined based on optical excitation, and possibly RF excitation, in a corresponding way to that described above with NV diamond material.

Figure 6:
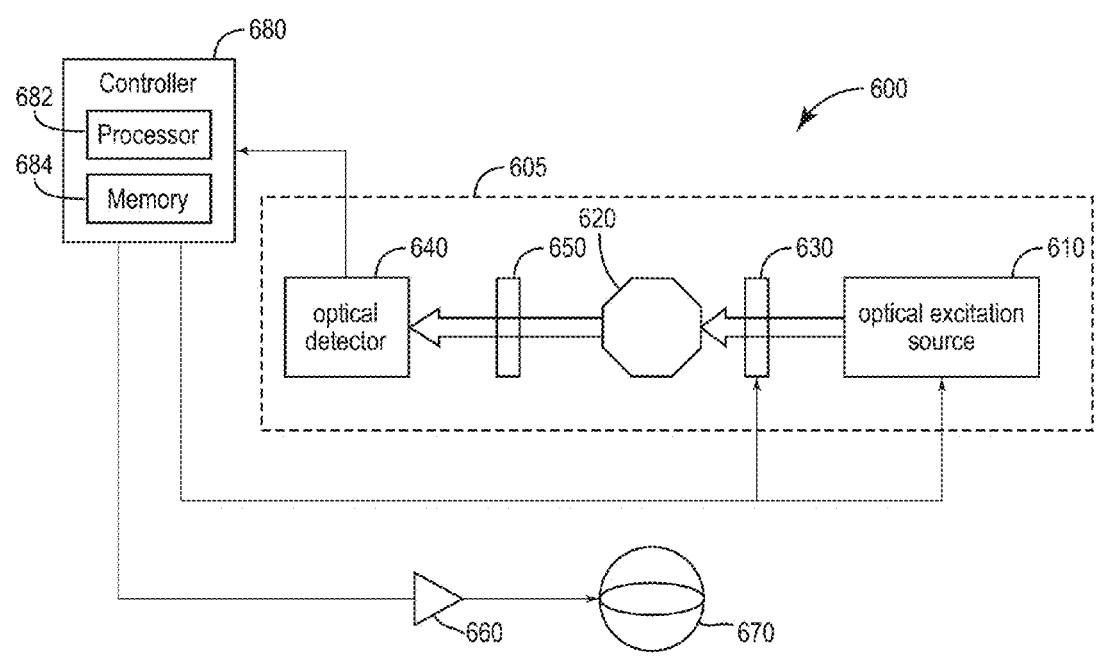
FIG. 6 is a schematic diagram illustrating a magnetic field detection system according to an embodiment.

FIG. 6 is a schematic diagram of a system 600 for a magnetic field detection system according to an embodiment. The system 600 includes an optical excitation source 610, which directs optical excitation to an NV diamond material 620 with NV centers, or another magneto-optical defect center material with magneto-optical defect centers. An RF excitation source 630 provides RF radiation to the NV diamond material 620. A magnetic field generator 670 generates a magnetic field, which is detected at the NV diamond material 620.

The magnetic field generator 670 may generate magnetic fields with orthogonal polarizations, for example. In this regard, the magnetic field generator 670 may include two or more magnetic field generators, such as two or more Helmholtz coils. The two or more magnetic field generators may be configured to provide a magnetic field having a predetermined direction, each of which provide a relatively uniform magnetic field at the NV diamond material 620. The predetermined directions may be orthogonal to one another. In addition, the two or more magnetic field generators of the magnetic field generator 670 may be disposed at the same position, or may be separated from each other. In the case that the two or more magnetic field generators are separated from each other, the two or more magnetic field generators may be arranged in an array, such as a one-dimensional or two-dimensional array, for example.

The system 600 may be arranged to include one or more optical detection systems 605, where each of the optical detection systems 605 includes the optical detector 640, optical excitation source 610, and NV diamond material 620. Furthermore, the magnetic field generator 670 may have a relatively high power as compared to the optical detection systems 605. In this way, the optical systems 605 may be deployed in an environment that requires a relatively lower power for the optical systems 605, while the magnetic field generator 670 may be deployed in an environment that has a relatively high power available for the magnetic field generator 670 so as to apply a relatively strong magnetic field.

The system 600 further includes a controller 680 arranged to receive a light detection signal from the optical detector 640 and to control the optical excitation source 610, the RF excitation source 630, and the second magnetic field generator 675. The controller may be a single controller, or multiple controllers. For a controller including multiple controllers, each of the controllers may perform different functions, such as controlling different components of the system 600. The second magnetic field generator 675 may be controlled by the controller 680 via an amplifier 660, for example.

The RF excitation source 630 may be a microwave coil, for example. The RF excitation source 630 is controlled to emit RF radiation with a photon energy resonant with the transition energy between the ground $m_s=0$ spin state and the $m_s=\pm 1$ spin states as discussed above with respect to FIG. 3.

The optical excitation source 610 may be a laser or a light emitting diode, for example, which emits light in the green, for example. The optical excitation source 610 induces fluorescence in the red from the NV diamond material 620, where the fluorescence corresponds to an electronic transition from the excited state to the ground state. Light from the NV diamond material 620 is directed through the optical filter 650 to filter out light in the excitation band (in the green, for example), and to pass light in the red fluorescence band, which in turn is detected by the optical detector 640. The optical excitation light source 610, in addition to exciting fluorescence in the NV diamond material 620, also serves to reset the population of the $m_s=0$ spin state of the ground state $^3A_2$ to a maximum polarization, or other desired polarization.

The controller 680 is arranged to receive a light detection signal from the optical detector 640 and to control the optical excitation source 610, the RF excitation source 630, and the second magnetic field generator 675. The controller may include a processor 682 and a memory 684, in order to control the operation of the optical excitation source 610, the RF excitation source 630, and the second magnetic field generator 675. The memory 684, which may include a nontransitory computer readable medium, may store instructions to allow the operation of the optical excitation source 610, the RF excitation source 630, and the second magnetic field generator 675 to be controlled. That is, the controller 680 may be programmed to provide control.

Ramsey Pulse Sequence Overview

According to certain embodiments, the controller 680 controls the operation of the optical excitation source 610, the RF excitation source 630, and the magnetic field generator 670 to perform Optically Detected Magnetic Resonance (ODMR). The component of the magnetic field Bz along the NV axis of NV centers aligned along directions of the four different orientation classes of the NV centers may be determined by ODMR, for example, by using an ODMR pulse sequence according to a Ramsey pulse sequence. The Ramsey pulse sequence is a pulsed RF-pulsed laser scheme that measures the free precession of the magnetic moment in the NV diamond material 620 and is a technique that quantum mechanically prepares and samples the electron spin state.

Figure 7:
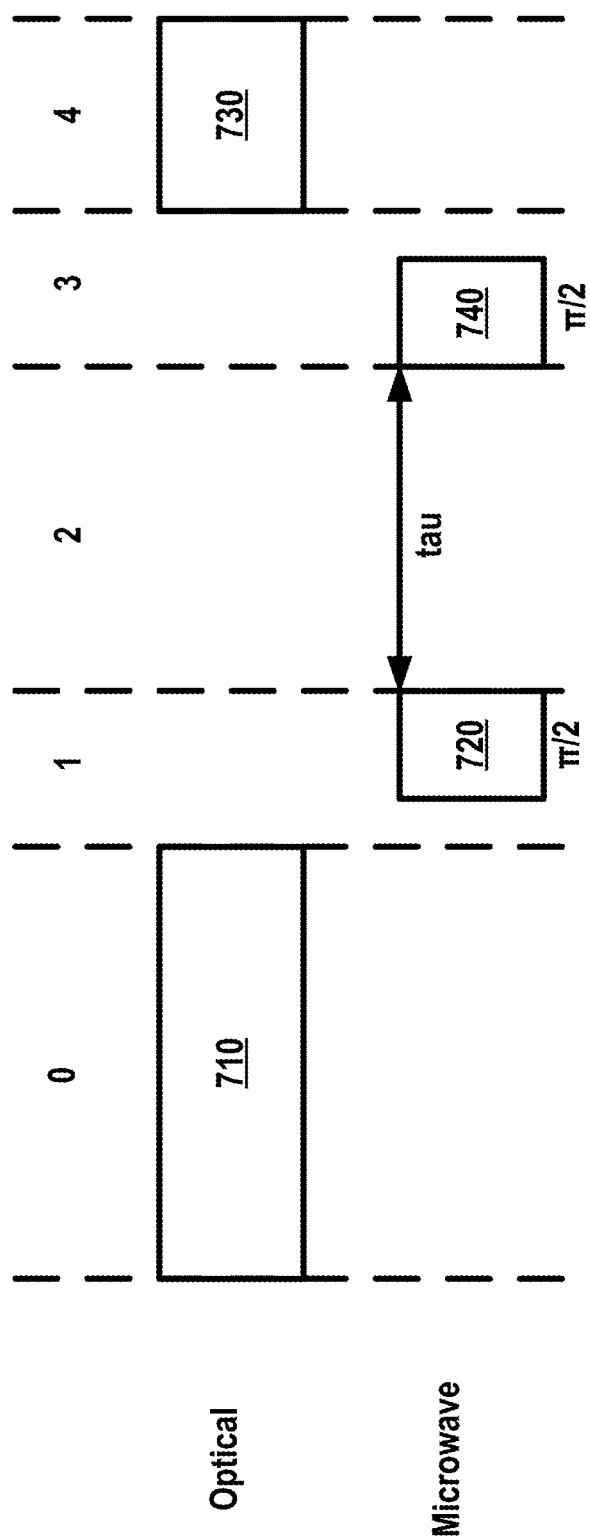
FIG. 7 is a schematic illustrating a Ramsey sequence of optical excitation pulses and RF excitation pulses according to an operation of the system of FIG. 6.

FIG. 7 is a schematic diagram illustrating the Ramsey pulse sequence. As shown in FIG. 7, a Ramsey pulse sequence includes optical excitation pulses and RF excitation pulses over a five-step period. In a first step, during a period 0, a first optical excitation pulse 710 is applied to the system to optically pump electrons into the ground state (i.e., $m_s=0$ spin state). This is followed by a first RF excitation pulse 720 (in the form of, for example, a microwave (MW)

π/2 pulse) during a period 1. The first RF excitation pulse 720 sets the system into superposition of the $m_s=0$ and $m_s=+1$ spin states (or, alternatively, the $m_s=0$ and $m_s=-1$ spin states, depending on the choice of resonance location). During a period 2, the system is allowed to freely precess (and dephase) over a time period referred to as tau (τ). During this free precession time period, the system measures the local magnetic field and serves as a coherent integration. Next, a second RF excitation pulse 740 (in the form of, for example, a MW π/2 pulse) is applied during a period 3 to project the system back to the $m_s=0$ and $m_s=+1$ basis. Finally, during a period 4, a second optical pulse 730 is applied to optically sample the system and a measurement basis is obtained by detecting the fluorescence intensity of the system. The RF excitation pulses applied to the system 600 are provided at a given RF frequency, which correspond to a given NV center orientation. The Ramsey pulse sequence shown in FIG. 12 may be performed multiple times, wherein each of the MW pulses applied to the system during a given Ramsey pulse sequence includes a different frequency that respectively corresponds to a different NV center orientation.

The theoretical measurement readout from a Ramsey pulse sequence may be defined as equation (1) below:

$$1 - e^{\frac{\tau}{T_2^*}} * \left(\frac{\omega_{res}}{\omega_{eff}}\right)^2 * \sum_{m=-1}^{1} \cos((2\pi(\Delta + m*a_n))*(\tau + \theta)) \quad (1)$$

In equation (1) above, τ represents the free precession time, $T_2^*$ represents spin dephasing due to inhomogeneities present in the system 600, $\omega_{res}$ represents the resonant Rabi frequency, $\omega_{eff}$ represents the effective Rabi frequency, $\alpha_n$ represents the hyperfine splitting of the NV diamond material 620 (~2.14 MHz), Δ represents the MW detuning, and θ represents the phase offset.

Figure 8A:
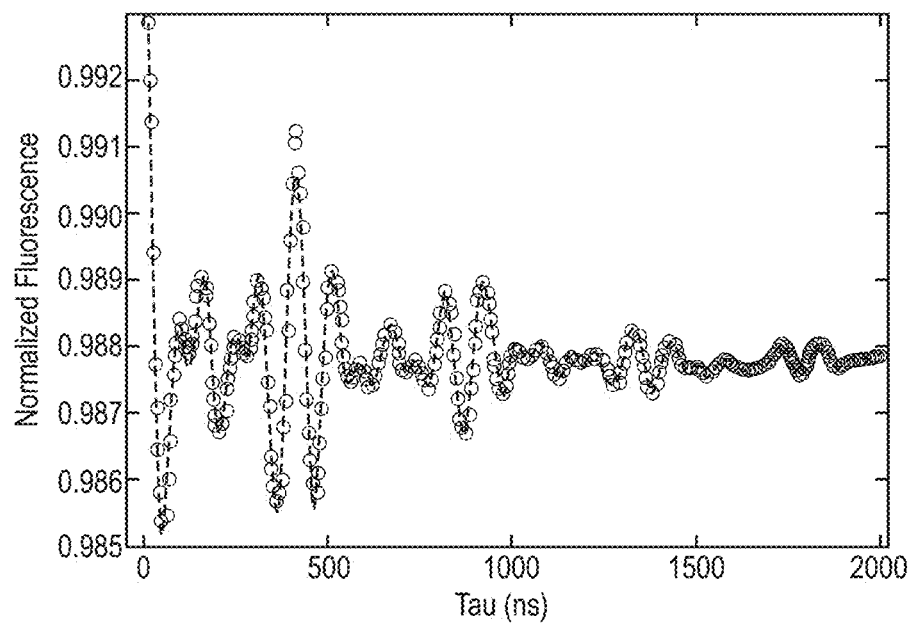
FIG. 8A is a free induction decay curve where a free precession time $\tau$ is varied using the Ramsey sequence of FIG. 7.
Figure 8B:
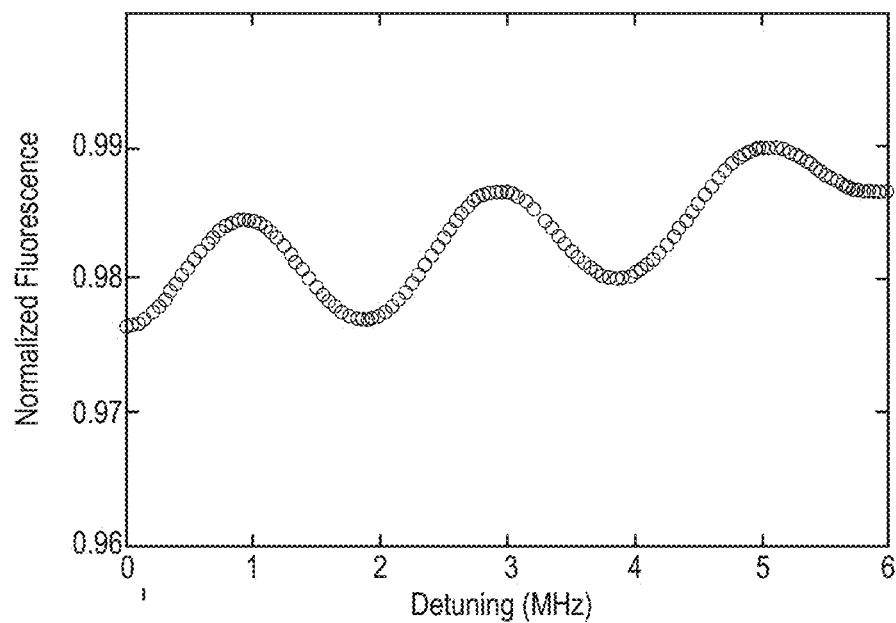
FIG. 8B is a magnetometry curve where a RF detuning frequency $\Delta$ is varied using the Ramsey sequence of FIG. 7.

When taking a measurement based on a Ramsey pulse sequence, the parameters that may be controlled are the duration of the MW π/2 pulses, the frequency of the MW pulse (which is referenced as the frequency amount detuned from the resonance location, Δ), and the free precession time τ. FIGS. 8A and 8B show the effects on the variance of certain parameters of the Ramsey pulse sequence. For example, as shown in FIG. 8A, if all parameters are kept constant except for the free precession time τ, an interference pattern, known as the free induction decay (FID), is obtained. The FID curve is due to the constructive/destructive interference of the three sinusoids that correspond to the hyperfine splitting. The decay of the signal is due to inhomogeneous dephasing and the rate of this decay is characterized by $T_2^*$ (characteristic decay time). In addition, as shown in FIG. 8B, if all parameters are kept constant except for the microwave detuning Δ, a magnetometry curve is obtained. In this case, the x-axis may be converted to units of magnetic field through the conversion 1 nT=28 Hz in order to calibrate for magnetometry.

By varying both τ and Δ, a two-dimensional FID surface plot may be constructed, an example of which is shown in FIG. 9A. The FID surface plot includes several characteristics that can elucidate optimization of the controllable parameters of the Ramsey sequence. For example, in FIG. 9A, the FID surface plot is generated using a $T_2^*$ of about 750 ns and a resonant Rabi frequency of about 6.25 MHz. The horizontal slices of FIG. 9A represent individual FID curves (e.g., FIG. 8A), while the vertical slices represent magnetometry curves (e.g., FIG. 8B). As shown in FIG. 9A, FID curves of higher fundamental frequency occur at greater detuning. Thus, higher detuning frequencies may be used to fit $T_2^*$ for diamond characterization. In addition, magnetometry curves, such as that shown in FIG. 8B, demonstrate that certain areas generate greater sensitivities. In particular, by taking the gradient of a two-dimensional FID surface plot, discreet optimal free precession intervals may be identified that present greater sensitivities, the best of which will be determined by $T_2^*$. FIG. 9B shows the gradient of the two-dimensional FID surface plot of FIG. 9A. In FIG. 9B, for the particular $T_2^*$ used (i.e., about 750 ns), operating at around 900 ns (indicated by area 2 of FIG. 9B) will yield the greatest sensitivity. However, shorter $T_2^*$ will show better performance between about 400 ns and about 500 ns (indicated by area 1 of FIG. 9B), while longer $T_2^*$ will show better performance at around 1400 ns (indicated by area 3 of FIG. 9B). These strong interference regions indicated by a plot such as that shown in FIG. 9B allow for the optimization of τ that will yield greater measurement sensitivity.

In addition, while the decay in the horizontal axis of FIG. 9B is characterized by $T_2^*$ the decay in the vertical axis is characterized by the ratio of the resonant Rabi frequency $\omega_{res}$ (described in more detail below) to the effective Rabi frequency $\omega_{eff}$. The effective Rabi frequency may be defined by equation (2) below:

$$\omega_{eff} := \sqrt{\omega_{res}^2 + \Delta^2} \quad (2)$$

Thus, the ratio of the resonant Rabi frequency and the effective Rabi frequency may be expressed in terms of the resonant Rabi frequency, as follows:

$$\frac{\omega_{res}}{\omega_{eff}} = \frac{\omega_{res}}{\sqrt{\omega_{res}^2 + \Delta^2}} \quad (3)$$

As shown in equation (3) above, when the resonant Rabi frequency $\omega_{res}$ is much greater than the MW detuning Δ, the ratio of the resonant Rabi frequency to the effective Rabi frequency will be about equal to 1. The decay shown in the vertical axis of FIG. 9B may be partially controlled by RF excitation power. As will be described in greater detail below, as the RF excitation power increases, a greater resonant Rabi frequency may be realized, while also decreasing the percent change in the effective Rabi frequency due to detuning. Thus, according to certain embodiments, magnetometry measurements are operated in regions that are dominated by the resonant Rabi frequency (such that the ratio of equation (3) is close to 1) in order to achieve maximum contrast.

Measurement Sequence

Using the above observations, a general three-step approach may be used to obtain highly sensitive magnetometry measurements. In this general approach, a first step is performed to verify the resonant Rabi frequency $\omega_{res}$. In a second step, the inhomogeneous dephasing $T_2^*$ of the system is measured. Finally, using the measurements obtained in the first and second steps, the parameter space of equation (1) is optimized and a highly sensitivity magnetometry measurement is performed. These three steps are described in more detail below.

Measuring the Resonant Rabi Frequency

Figure 10:
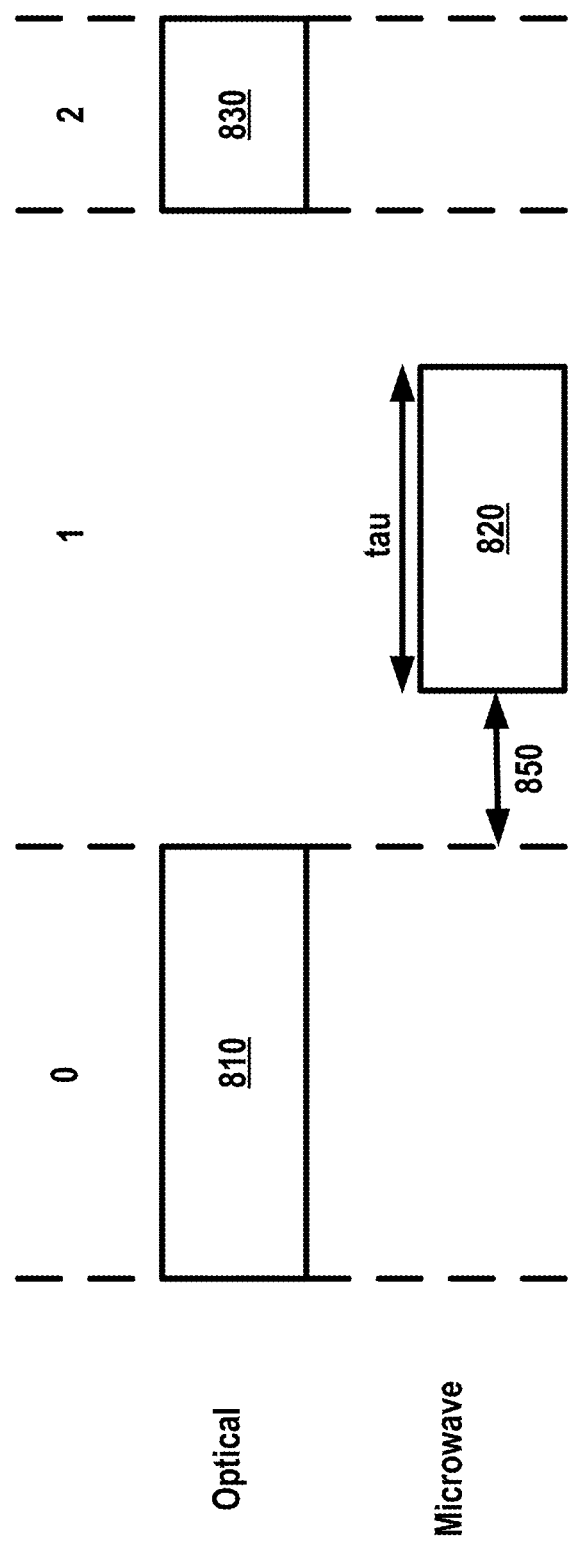
FIG. 10 is a schematic illustrating a Rabi sequence of optical excitation pulses and RF pulses according to an operation of the system of FIG. 6.

To verify the resonant Rabi frequency, first, a bias magnetic field using the magnetic field generator 670 is applied to the system 600 such that the outermost resonance of the fluorescence intensity response is separated, while the three remaining resonances for the other axes remain overlapping. Next, either a CW-CW sweep or a single π pulse sweep is applied to identify the resonance RF frequency that corresponds to the axis of interest (i.e., the outermost resonance). Then, while tuned to this resonance, a series of Rabi pulses is applied. FIG. 10 shows an example of a Rabi pulse sequence. As shown in FIG. 10, three periods of optical and RF excitation pulses are applied. First, a first optical excitation pulse 810 is applied, which is followed by a RF excitation pulse 820 (e.g., a MW pulse). The Rabi pulse sequence is then completed by a second optical excitation pulse 830. During application of the series of Rabi pulses, the time interval in which the RF pulse is applied (shown as tau τ in FIG. 10, but this tau τ should be distinguished from the free precession interval τ in a Ramsey pulse sequence) is varied. During this process, a constant optical duty cycle is maintained to minimize thermal effects in the system. This may be achieved with the use of a variable "guard" window, shown as the period 850 in FIG. 10, between the first optical pulse 810 and the MW pulse 820. The guard window 850 helps to ensure that the first optical pulse 810 is completely off by the time the MW pulse 820 is applied, thus preventing any overlap between the two pulses and preventing the optical pulse from partially re-initializing the NV diamond material while the MW pulse 820 is being applied.

Figure 11:
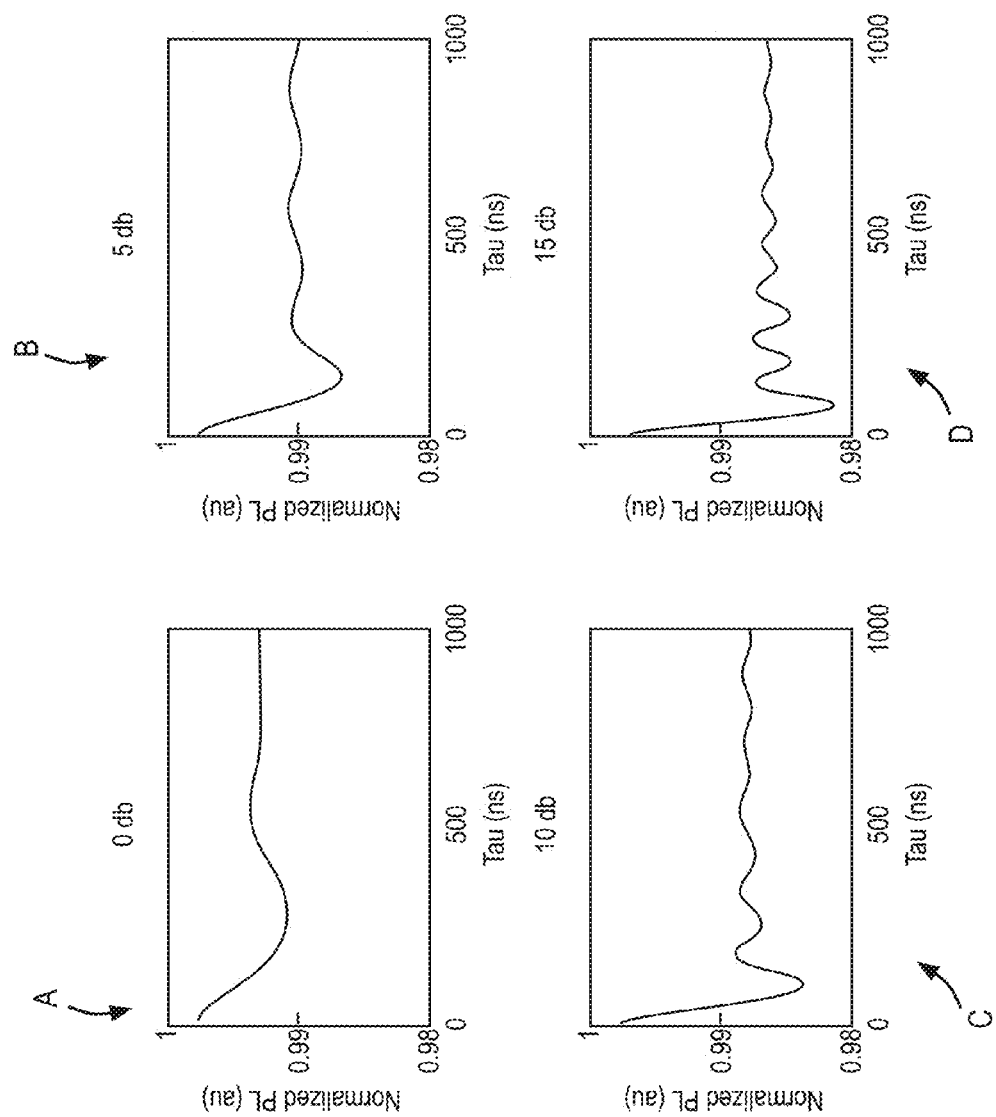
FIG. 11 is a comparison of graphs showing resonant Rabi frequencies according to a power of RF excitation applied to the system of FIG. 6.

After application of the Rabi pulses, the resonant Rabi frequency $\omega_{res}$ is defined by the frequency of the resulting curve. FIG. 11 shows measured curves A-D after the application of the Rabi pulses using varying RF excitation power (e.g., MW power). As shown by the differences in the frequency of curves A-D, by increasing the MW power applied to the system 600, the resonant Rabi frequency $\omega_{res}$ obtained also increases. Thus, to obtain practical Rabi frequencies (e.g., greater than 5 MHz), substantial amounts of MW power should be used. In some embodiments, sufficient MW power may be applied to ensure that application of the pulses is kept short, while, at the same time, the MW power may be limited to avoid saturation. In certain embodiments, a power of about 10 watts may be applied. Depending on the RF excitation source 630 used to apply the RF excitation, the necessary power requirements to achieve practical Rabi frequencies may be difficult to achieve. In certain embodiments, however, a small loop antenna (e.g., an antenna having a loop size of about 2 mm in diameter) may be used as the RF excitation source 630. By applying a small loop antenna, a high MW power may be achieved while significantly reducing the required antenna power due to the ability to position the antenna in closer proximity to the NV diamond material 620. Thus, the increase in MW power achieved by the small loop antenna allows for an increase in the resonant Rabi frequency $\omega_{res}$. The data obtained during this step of the measurement process is used to determine the π/2 pulse necessary to perform the Ramsey pulse sequence (described below). In this case, π may be defined as the first minimum of the Rabi curve obtained (e.g., curve D in FIG. 11).

Measuring T2*

In a second step of the measurement process, using the π/2 pulse determined by the resonant Rabi frequency and the resonance location obtained during the first step above, measurements of the inhomogeneous dephasing $T_2^*$ of the system are obtained. Measurements are performed similar to the Rabi measurements described above, except a Ramsey pulse sequence is used. As described above with reference to the Ramsey pulse sequence, tau τ denotes the free precession time interval in this step.

In estimating $T_2^*$, the detune frequency Δ is set to be relatively high, in certain embodiments. As noted above, larger detune frequencies cause higher fundamental frequencies (see, e.g., FIG. 9A), thus allowing for greater contrast, making the data easier to fit. In some embodiments, the detune frequency Δ may be set to about 10 MHz. However, for relatively large $T_2^*$, smaller detune frequencies may be used. FIG. 8A shows one example of an FID curve that may be used to obtain $T_2^*$, where the detune frequency was set to about 10 MHz. By determining $T_2^*$ from an FID curve such as that shown in FIG. 8A, the optimal free precession time τ may be determined based on the strong interference regions discussed above with reference to FIG. 9B. In addition, in certain embodiments, a small range of τ's are also collected on either side of the optimally determined free precession time due to the theta term in equation (1).

Magnetometry Measurements

In the final step of the measurement process, measurement of the fluorescence intensity response is performed using the parameters obtained in the above steps. As discussed above, the identified resonant Rabi frequency gives the duration of the MW π/2 pulse (used as RF excitation pulses 720 and 740), and the FID curve gives $T_2^*$, which is used to determine the region of optimal free precession time τ. It should be noted that, during this final step, in some embodiments, the optical pulse used for optical polarization of the system and the optical pulse used for measurement readout may be merged into one pulse during application of a series of Ramsey sequences.

In addition, in order to increase sensitivity, measurements made in a second per fixed measurement error may be increased in certain embodiments. Thus, to maximize sensitivity, the total length of a single measurement cycle should be minimized, which may be achieved through the use of higher optical powers of the optical excitation source 610. Accordingly, given the above, in certain embodiments, the optical power of the optical excitation source 610 may be set to about 1.25 W, the MW π/2 pulse may be applied for about 50 ns, the free precession time τ may be about 420 ns, and the optical excitation pulse duration may be about 50 μs. Moreover, "guard" windows may be employed before and after the MW π/2 pulses, which may be set to be about 2.28 μs and 20 ns in duration, respectively.

In conventional measurement processes, the curve in the intensity response is typically only measured once to obtain the slope and fine-tuned frequency, and additional measurements are only taken at the optimal detuning frequency, while the fluorescence signal is monitored. However, the system may experience drift caused by, for example, optical excitation heating (e.g., laser-induced heating) and/or strain, which can contribute to imprecision and error during the measurement process. Tracking a single spin resonance does not properly account for the translation in response curves due to thermal effects. Thus, according to some embodiments, to account for nonlinearities over a larger band of magnetic fields, data obtained from the measuring process is saved in real-time and sensitivity is determined offline to minimize time between measurements. In addition, magnetometry curves are collected on both the $m_s=+1$ and $m_s=-1$ spin states for the same NV symmetry axis. For example, in certain embodiments, RF excitation pulses during the Ramsey sequences may be alternatively applied at low resonance (i.e., resonance frequency of the $m_s=-1$ spin state) and at high resonance (i.e., resonance frequency of the $m_s=+1$ spin state) to obtain measurements associated with each of the spin states ($m_s=-1$ and $m_s=+1$ spin states). Thus, two magnetometry curves (e.g., FIG. 8B) may be obtained for both the positive and negative spin states. By applying the RF pulses at separate frequencies, translation due to temperature and/or strain effects may be compensated. The magnetic field measurements may be made using equations (4) and (5) below, where I represents the normalized intensity of the fluorescence (e.g., red) and $m_1$ and $m_2$ represent the measurements taken for each of the $m_s=+1$ and $m_s=-1$ spin states for a given axis:

$$m = \frac{dI}{df} \quad (4)$$

$$dB = \frac{h}{2g\mu_b}\left(\frac{dI_1}{m_1} \mp \frac{dI_2}{m_2}\right) \quad (5)$$

For measurements obtained on opposite slopes, plus is used in equation (5). If the peaks of the $m_s=+1$ and $m_s=-1$ spin states translate, the intensity response will occur in opposite directions. If, on the other hand, the peaks separate outward due to a change in the magnetic field, then the intensity change will agree to yield the appropriate dB measurement. Thus, by obtaining measurements of the curves for both the $m_s=+1$ and $m_s=-1$ spin states for the same NV symmetry axis, changes due to temperature and changes due to the magnetic field may be separated. Accordingly, translation shifts due to temperature and/or strain effects may be accounted for, allowing for a more accurate calculation of the magnetic field contribution on the system.

Signal Processing

Figure 12:
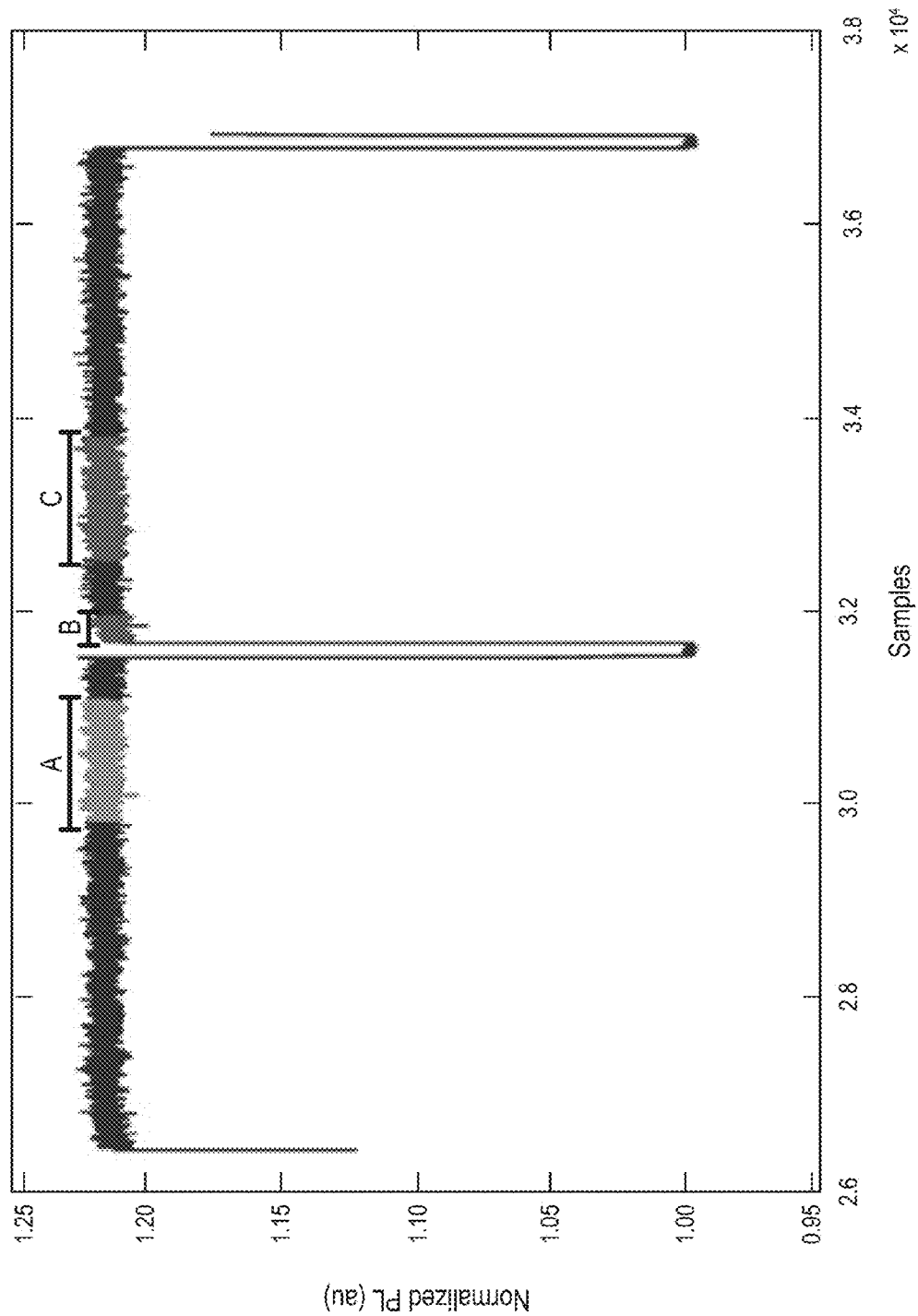
FIG. 12 is a graph showing raw pulse data collected during an operation of the system of FIG. 6.

Processing may be performed on the raw data obtained to acquire clean images of the measurements obtained during each of the steps described above. FIG. 12 shows an example of a raw pulse data segment that may be obtained during a given measurement cycle. Theoretically, the signal is defined as the first 300 ns of an optical excitation pulse. However, this definition applies at optical power densities that are near saturation. As optical power density decreases from saturation, the useful part of the signal may extend further in time. Currently, in conventional processing methods, the end of the pulse, when the system has been polarized, is referenced in order to account for power fluctuations in the optical excitation source (e.g., the laser). This is shown in FIG. 12, where the signal may be obtained using a first reference window or period defined by C minus a signal window or period defined by B (i.e., signal=C−B), which are both referenced after the MW pulse. According to certain embodiments, however, in order to increase sensitivity, the reference may be extended to include a second reference window or period defined by A before the microwave pulse $$\left(i.e., \text{signal} = \frac{A+C}{2} - B\right).$$

The samples within the windows or periods (i.e., A, B, and C) may be averaged to obtain a mean value of the signal contained within the respective window or period. Furthermore, in some embodiments, the value of the windows or periods (e.g., signal window B) may be determined using a weighted mean. In addition, in certain embodiments, the first and second reference windows are equally spaced from the signal window, as shown in FIG. 12. This extension of referencing allows for better estimation of the optical excitation power during the acquisition of the signal and an overall increase in sensitivity of the system.

The embodiments of the inventive concepts disclosed herein have been described in detail with particular reference to preferred embodiments thereof, but it will be understood by those skilled in the art that variations and modifications can be effected within the spirit and scope of the inventive concepts.

What is claimed is:

1. A system for magnetic detection, comprising:
a nitrogen vacancy (NV) diamond material comprising a plurality of NV centers;
a radio frequency (RF) excitation source configured to provide RF excitation to the NV diamond material;
an optical excitation source configured to provide optical excitation to the NV diamond material;
an optical detector configured to receive an optical signal emitted by the NV diamond material;
a magnetic field generator configured to generate a magnetic field applied to the NV diamond material; and
a controller configured to:
control the optical excitation source and the RF excitation source to apply a first pulse sequence comprising two optical excitation pulses and two RF excitation pulses to the NV diamond material;
receive a first light detection signal from the optical detector based on an optical signal emitted by the NV diamond material due to the first pulse sequence;
measure a first value of the first light detection signal at a first reference period, the first reference period being before a period of the first light detection signal associated with the two RF excitation pulses of the first pulse sequence provided to the NV diamond material;
measure a second value of the first light detection signal at a second reference period, the second reference period being after the period of the first light detection signal associated with the two RF excitation pulses of the first pulse sequence provided to the NV diamond material;
compute a first measurement based on the measured first and second values of the first light detection signal;
control the optical excitation source and the RF excitation source to apply a second pulse sequence comprising two optical excitation pulses and two RF excitation pulses to the NV diamond material;
receive a second light detection signal from the optical detector based on an optical signal emitted by the NV diamond material due to the second pulse sequence;
measure a first value of the second light detection signal at a first reference period, the first reference period being before a period of the second light detection signal associated with the two RF excitation pulses of the second pulse sequence provided to the NV diamond material;
measure a second value of the second light detection signal at a second reference period, the second reference period being after the period of the second light detection signal associated with the two RF excitation pulses of the second pulse sequence provided to the NV diamond material; and compute a second measurement based on the measured first and second values of the second light detection signal, wherein the first measurement is based on a high resonance frequency of the NV diamond material, and wherein the second measurement is based on a low resonance frequency of the NV diamond material.

2. The system of claim 1, wherein the high resonance frequency and the low resonance frequency are resonance frequencies associated with an axis of an NV center of the NV diamond material.

3. The system of claim 1, wherein the controller is further configured to compute a change in an external magnetic field acting on the NV diamond material based on the first and second measurements.

4. The system of claim 1, wherein the two RF excitation pulses of the first pulse sequence are applied at a frequency detuned from the high resonance frequency of the NV diamond material.

5. The system of claim 1, wherein the two RF excitation pulses of the second pulse sequence are applied at a frequency detuned from the low resonance frequency of the NV diamond material.

6. The system of claim 1, wherein the RF excitation source is a microwave antenna.

7. The system of claim 1, wherein the controller is configured to apply one of the two optical excitation pulses, followed by the two RF excitation pulses, and followed by the other of the two optical excitation pulses during each of the first pulse sequence and the second pulse sequence.

8. The system of claim 1, wherein the controller is further configured to measure a third value of the first light detection signal at a signal period, the signal period being after the first reference period and before the second reference period of the first light detection signal.

9. The system of claim 8, wherein the controller is further configured to compute the first measurement based on a difference between the average of the first and second values and the third value of the first light detection signal.

10. A system for magnetic detection, comprising:
a nitrogen vacancy (NV) diamond material comprising a plurality of NV centers;
a radio frequency (RF) excitation source configured to provide RF excitation to the NV diamond material;
an optical excitation source configured to provide optical excitation to the NV diamond material;
an optical detector configured to receive an optical signal emitted by the NV diamond material;
a magnetic field generator configured to generate a magnetic field applied to the NV diamond material; and
a controller configured to:
control the optical excitation source and the RF excitation source to apply a pulse sequence comprising two optical excitation pulses and at least one RF excitation pulse to the NV diamond material;
receive a light detection signal from the optical detector based on an optical signal emitted by the NV diamond material due to the pulse sequence;
measure a first value of the light detection signal at a first reference period, the first reference period being before a period of the light detection signal associated with the at least one RF excitation pulse provided to the NV diamond material;
measure a second value of the light detection signal at a second reference period, the second reference period being after the period of the light detection signal associated with the at least one RF excitation pulse provided to the NV diamond material; and
compute a measurement signal based on the measured first and second values.

11. The system of claim 10, wherein the controller is further configured to measure the first value and the second value based on an average of values of the light detection signal within the first reference period and the second reference period.

12. The system of claim 10, wherein the controller is further configured to compute the measurement signal based on the average of the first value and the second value.

13. The system of claim 10, wherein the controller is further configured to measure a third value of the light detection signal at a signal period, the signal period being after the first reference period and before the second reference period.

14. The system of claim 13, wherein the controller is further configured to compute the measurement signal based on a difference between the average of the first and second values and the third value.

15. The system of claim 10, wherein the first reference period is associated with one of the two optical excitation pulses and the second reference period is associated with the other of the two optical excitation pulses.

16. A system for magnetic detection, comprising:
a nitrogen vacancy (NV) diamond material comprising a plurality of NV centers;
a radio frequency (RF) excitation source configured to provide RF excitation to the NV diamond material;
an optical excitation source configured to provide optical excitation to the NV diamond material;
an optical detector configured to receive an optical signal emitted by the NV diamond material;
a magnetic field generator configured to generate a magnetic field applied to the NV diamond material; and
a controller configured to:
control the optical excitation source and the RF excitation source to apply a first pulse sequence comprising two optical excitation pulses and two RF excitation pulses to the NV diamond material;
receive a first light detection signal from the optical detector based on an optical signal emitted by the NV diamond material due to the first pulse sequence;
compute a first measurement based on the first light detection signal;
control the optical excitation source and the RF excitation source to apply a second pulse sequence comprising two optical excitation pulses and two RF excitation pulses to the NV diamond material;
receive a second light detection signal from the optical detector based on an optical signal emitted by the NV diamond material due to the second pulse sequence; and
compute a second measurement based on the second light detection signal, wherein the first measurement is based on a high resonance frequency of the NV diamond material, and wherein the second measurement is based on a low resonance frequency of the NV diamond material.

17. The system of claim 16, wherein the high resonance frequency and the low resonance frequency are resonance frequencies associated with an axis of an NV center of the NV diamond material.

18. The system of claim 16, wherein the two RF excitation pulses of the first pulse sequence are applied at a frequency detuned from the high resonance frequency of the NV diamond material.

19. The system of claim 16, wherein the two RF excitation pulses of the second pulse sequence are applied at a frequency detuned from the low resonance frequency of the NV diamond material.

20. The system of claim 16, wherein the controller is further configured to compute a change in an external magnetic field acting on the NV diamond material based on the first and second measurements.

* * * * *